US010598615B2

(12) United States Patent
Kleine et al.

(10) Patent No.: US 10,598,615 B2
(45) Date of Patent: Mar. 24, 2020

(54) METHOD OF ADJUSTING THE PRIMARY SIDE OF AN X-RAY DIFFRACTOMETER

(71) Applicant: Incoatec GmbH, Geesthacht (DE)

(72) Inventors: Andreas Kleine, Hamburg (DE); Nima Bashiry, Hamburg (DE); Detlef Bahr, Karlsruhe (DE); Carsten Michaelsen, Artlenburg (DE)

( * ) Notice: Subject to any disclaimer, the term of this patent is extended or adjusted under 35 U.S.C. 154(b) by 549 days.

(21) Appl. No.: 15/357,642

(22) Filed: Nov. 21, 2016

(65) Prior Publication Data

US 2017/0160212 A1    Jun. 8, 2017

(30) Foreign Application Priority Data

Dec. 3, 2015    (DE) .......................... 10 2015 224 143

(51) Int. Cl.

| | |
|---|---|
| *G01N 23/20008* | (2018.01) |
| *G21K 1/06* | (2006.01) |
| *G01T 7/00* | (2006.01) |
| *G21K 1/02* | (2006.01) |
| *H05G 1/02* | (2006.01) |

(Continued)

(52) U.S. Cl.
CPC ....... *G01N 23/20008* (2013.01); *G01T 7/005* (2013.01); *G21K 1/06* (2013.01);
(Continued)

(58) Field of Classification Search
CPC .... G01T 1/00; G01T 1/02; G01T 1/16; G01T 1/20; G01T 1/2006; G01T 1/2018; G01T 1/24; G01T 1/29; G01T 1/2921; G01T 1/2928; G01T 7/00; G01T 7/005; G21K 1/00; G21K 1/06; H05G 1/00; H05G 1/02; H05G 1/26; H01J 35/00; H01J 35/02; H01J 35/025; H01J 35/16; H01J 3/00; H01J 3/14; H01J 3/16; H01J 29/58; H01J 29/60; H01J 37/00; H01J 37/21; H01J 37/22; H01J 37/226; H01J 37/244; H01J 37/26;
(Continued)

(56) References Cited

U.S. PATENT DOCUMENTS

| | | |
|---|---|---|
| 5,541,856 A | 7/1996 | Hammermeister |
| 5,896,200 A | 4/1999 | Shu |

(Continued)

FOREIGN PATENT DOCUMENTS

| | | |
|---|---|---|
| DE | 112013002039 A1 | 1/2015 |
| DE | 112013002039 T5 | 1/2015 |

(Continued)

*Primary Examiner* — Anastasia Midkiff
(74) *Attorney, Agent, or Firm* — Benoit & Côté Inc.

(57) ABSTRACT

A method for adjusting a primary side of an X-ray diffractometer wherein the primary side comprises a collimator, X-ray optics, an X-ray source, in particular an X-ray tube, wherein the collimator, the X-ray optics and the X-ray source are mounted directly or indirectly on a base structure, and wherein the orientation and position of the X-ray optics and the position of the X-ray source are adjusted relative to the base structure, wherein the method is characterized in that the orientation and position of the X-ray optics and the position of the X-ray tube relative to the base structure are measured and set at predetermined target values, so that with these set target values, X-ray radiation emanating from the X-ray source and conditioned by the X-ray optics is detectable at the output end of the collimator.

25 Claims, 17 Drawing Sheets

(51) Int. Cl.
*H01J 37/22* (2006.01)

(52) U.S. Cl.
CPC ... *G01N 2223/056* (2013.01); *G01N 2223/32* (2013.01); *G21K 1/02* (2013.01); *H01J 37/22* (2013.01); *H01J 2237/061* (2013.01); *H01J 2237/1501* (2013.01); *H01J 2237/1502* (2013.01); *H01J 2237/2482* (2013.01); *H01J 2237/24578* (2013.01); *H05G 1/02* (2013.01)

(58) Field of Classification Search
CPC ...... H01J 37/261; H01J 37/265; H01J 37/295; H01J 2237/00; H01J 2237/045; H01J 2237/0451; H01J 2237/06; H01J 2237/061; H01J 2237/10; H01J 2237/15; H01J 2237/1501–1503; H01J 2237/245; H01J 2237/24578; H01J 2237/248; H01J 2237/2482; G01N 23/00; G01N 23/20; G01N 23/20008; G01N 23/20016
See application file for complete search history.

(56) References Cited

U.S. PATENT DOCUMENTS

| | | | |
|---|---|---|---|
| 6,041,099 A | 3/2000 | Gutman et al. | |
| 6,072,854 A * | 6/2000 | Kikuchi | C30B 15/00 378/71 |
| 7,511,902 B2 * | 3/2009 | Wings | G02B 7/1824 359/822 |
| 7,852,983 B2 * | 12/2010 | Mettendorf | G01N 23/207 378/71 |
| 7,983,388 B2 * | 7/2011 | Michaelsen | G21K 1/04 378/145 |
| 9,490,038 B2 | 11/2016 | Wakasaya et al. | |
| 2013/0259199 A1 * | 10/2013 | Ueji | G01N 23/20008 378/70 |
| 2013/0287178 A1 * | 10/2013 | Ryan | G21K 1/06 378/145 |
| 2013/0315375 A1 * | 11/2013 | Kleine | G01N 23/20008 378/71 |
| 2014/0023180 A1 | 1/2014 | Shu | |
| 2015/0098547 A1 | 4/2015 | Wakasaya | |
| 2015/0194287 A1 * | 7/2015 | Yun | H01J 35/08 378/44 |

FOREIGN PATENT DOCUMENTS

| | | |
|---|---|---|
| EP | 1365231 A2 | 11/2003 |
| EP | 1365231 B1 | 11/2005 |
| EP | 1462794 B1 | 11/2007 |
| EP | 1925932 A1 | 5/2008 |

\* cited by examiner

METHOD OF ADJUSTING THE PRIMARY SIDE OF AN X-RAY DIFFRACTOMETER

BACKGROUND OF THE INVENTION

Field of the Invention

The invention relates to a method for adjusting the primary side of an X-ray diffractometer, wherein the primary side comprises a collimator, an X-ray optics, an X-ray source, in particular an X-ray tube, wherein the collimator, the X-ray optics and the X-ray source are mounted directly or indirectly on a base structure, and wherein the orientation and position of the X-ray optics and the position of the X-ray source are adjusted relative to the base structure. Such a method may be used with the high-flux X-ray source known from EP 1 462 794 B1.

Description of the Related Art

X-ray diffractometry has been used for several decades for structural determination of matter with atomic resolution. The samples used in single crystal diffractometry are very small, often smaller than 100 µm. A typical single crystal diffractometer consists of the following components: X-ray tube for generating X-ray radiation, X-ray optics for conditioning the X-ray radiation, video microscope for centering the sample, exposure shutter for controlling the sample exposure, collimator for limiting the X-ray beam cross section, goniometer for orientation of the sample, primary beam attenuator for absorption of the direct beam and a planar detector for measuring the X-ray radiation diffracted by the sample.

Single crystal samples are often available only in a very small size; sample diameters of 100 µm or less are often encountered. To be able to perform measurements on such a small sample, a very precise conditioning and adjustment of the X-ray beam used are necessary.

X-ray beams for single crystal diffractometry are typically generated by an X-ray tube, whose source focus is imaged with X-ray optics, for example, a Montel mirror. The beam conditioned by the X-ray optic is directed through a collimator at the sample. The diffracted X-ray radiation is typically detected with a CCD camera. The sample is aligned by means of a goniometer. The X-ray tubes used in single crystal diffractometry are typically point-focus sources having a round optical focus with a diameter of approximately 50 µm. Stationary microfocus tubes, rotating anodes or liquid metal sources are used as the X-ray tubes.

The X-ray optic is usually a multi-layer X-ray mirror, so-called Montel mirror (e.g., U.S. Pat. No. 6,041,099 A). These are mirrors coated with gradient multi-layers. Due to the parabolic or paraboloid and/or elliptical or ellipsoid surface, they collimate and/or focus the X-ray radiation generated in the X-ray tube. In addition, these X-ray optics act as monochromators. In addition to the conditioning, the X-ray optics should also deflect the X-ray radiation onto the sample. Because of the small sample sizes in single crystal diffractometry, focusing X-ray optics are typically used for this purpose. The goal is to strike only the sample, despite the small sample size, because otherwise it leads to interference radiation and can have a negative effect on the quality of the data recorded by the planar detector.

Typical reflex widths of Montel mirrors are approximately 1 mrad (=0.057°) for Cu-K$\alpha$ X-ray radiation and/or approximately 0.5 mrad (=0.028°) for Mo-K$\alpha$ X-ray radiation. The angle range in which the mirrors reflect optimally is thus relatively narrow. The accurate adjustment of the source and/or source focus and the X-ray optic is therefore very important for typical focus sizes of 100 µm. Even a minor misalignment results in significantly inferior X-ray beam properties on the sample.

A single-hole aperture collimator has a pinhole aperture directly in front of the sample with the purpose of limiting the dimensions of the X-ray beam so that it illuminates only the sample. Typical pinhole aperture sizes here are 100 µm or 300 µm. A two-hole aperture collimator additionally has a pinhole aperture as close to the mirror output as possible, with the goal of reducing the maximum divergence of the X-ray beam. Typical pinhole aperture sizes are 500 µm at the input end and 300 µm at the output end (as seen in the direction of the beam).

The aforementioned components must then be adjusted relative to one another so that the X-ray optic optimally conditions the X-ray radiation output from the X-ray tube. The monochromatized X-ray beam shaped in two dimensions perpendicular to the beam propagation direction must additionally pass through the exposure shutter and the collimator, so that only the sample is illuminated with a maximum X-ray beam intensity. In addition, the X-ray beam exciting the sample must be aligned, so that it strikes the detector at a right angle.

For alignment of the components to one another, there are typically multiple adjusting screws on the components (e.g., U.S. Pat. No. 7,511,902 B2) according to the prior art. Furthermore, the adjustment process is carried out with X-ray radiation from the beginning. Since the safety requirements of today's X-ray systems have increased, adjustment work is allowed to be performed on the open beam only to a very restricted extent or not at all. Therefore, the diffractometer is typically situated in a radiation-safe radiation protection box, which ensures that the effective beam and/or the stray radiation emitted by the sample is/are blocked by suitable absorbers such as lead glass. Since the entire adjustment process is carried out with the help of X-ray radiation, the safety shutter must be closed for each adjustment strip, i.e., the actuation of an adjusting screw. A typical adjusting step thus involves the following procedure: 1) closing the safety shutter, 2) opening the door of the radiation safety box, 3) turning the adjusting screw, 4) closing the radiation safety box, 5) opening the safety shutter, 6) exposing the detector to the X-ray radiation, 7) reading out the detector and determining the count rate. The entire process typically takes 30 sec for a single adjustment step.

According to the prior art, the adjustment process on the primary side of a single crystal diffractometer includes the following typical steps: 1) adjusting the Montel mirror at the source focus with subsequent maximization of intensity, 2) adjusting the position and/or orientation of the X-ray beam and the collimator relative to one another, so that the X-ray radiation at the output end of the collimator is visible, 3) maximizing the intensity at the output end of the collimator, 4) aligning the X-ray beam with the sample. Now if the X-ray beam does not strike the detector at a right angle, the orientation of the Montel mirror must be changed to adjust the orientation of the X-ray beam accordingly. The adjustment process begins again at step 1). For each of the steps mentioned above, a plurality of the individual adjustment steps described above must be carried out on the respective adjusting screws. Finally, when the source focus is set for the Montel mirror, so that a maximum photon flux strikes the sample downstream from the collimator and strikes the detector at a right angle accordingly, then another sample crystal is measured.

With such an X-ray diffractometer design, adjustment of the primary side, i.e., the components before the sample, is difficult and time consuming and is usually done only by specially trained personnel of the diffractometer manufacturer. A relative adjustment of the components is carried out here essentially by maximizing the beam intensity at the output end in a plurality of individual adjustment steps. Based on safety regulations that are in effect, the individual adjustment steps may be carried out only when the X-ray beam is interrupted and/or the intensity measurements are performed only with the safety housing closed, which increases the adjustment effort to a particular extent. The adjustment is particularly problematical when no X-ray intensity passes through the collimator at the start of the adjustment because of a great misalignment. Since there are so many degrees of freedom, it is unclear which adjustment positions must be altered and in which way in order to achieve intensity again. The adjustment of the primary side of an X-ray diffractometer frequently takes several days.

In the typical adjustment process described above, steps 1) to 3) in particular are very time intensive and tedious. If there is a great misalignment between the source focus and the Montel mirror, the X-ray optics will reflect practically nothing. Since it is not clear without reflection on the X-ray optics where the fitting relative position and/or orientation is/are to be found, a great deal of time is required to find this through successive changes in the adjusting screws.

Since the X-ray optics and thus the X-ray beam conditioned by it have a relatively arbitrary position and orientation, the X-ray beam will in all probability not pass through a collimator mechanically positioned at the center. This means that the position and/or orientation of the X-ray beam and thus those of the X-ray optics must be adapted to the position of the collimator. By successively varying the beam position, thus the plane of the collimator aperture is scanned in a tedious process to detect an X-ray beam at the output end of the collimator. If this scanning takes place, for example, with a mirror housing according to U.S. Pat. No. 7,511,902 B2, then the adjusting screws act on the mirror backs by way of cams. The resulting movement thereof is thus not linear but instead is sinusoidal, which makes the change in position of the output beam from the alignment with the collimator aperture less intuitive and thus time consuming. Furthermore, it may happen that, for example, the Montel mirror is too far out of adjustment, so that the X-ray mirror no longer creates a reflection, which leads to a further loss of time.

Since each individual adjustment takes approximately 30 sec, one easily arrives at an adjustment expenditure according to the prior art amounting to several days. In the worst cases, the adjustment time may be as long as a week. This condition is not encouraging and makes clear the demand for an improved and simplified adjustment concept.

EP 1 462 794 B1 describes a high-flux X-ray source, in which an X-ray optic is mounted on an X-ray tube in a housing wherein the housing can be tilted and shifted with respect to the X-ray tube to adjust the housing by means of four adjusting screws. In addition, a collimator that can be tilted by means of two adjusting screws for the adjustment is mounted on the X-ray tube. The X-ray tube can also be adjusted vertically and horizontally by means of five screws with respect to a pedestal.

DE 11 2013 002 039 T5 describes an X-ray analyzer in which the position of a multi-layer mirror on the primary beam side can be adjusted by means of a motor. In addition, sensors to detect the position of optical X-ray components are proposed.

EP 1 365 231 A2 describes an X-ray diffractometer, wherein an X-ray source and a monochromator are firmly pre-assembled to each other.

SUMMARY OF THE INVENTION

The present invention provides a way to accelerate and simplify the adjustment of the primary side of an X-ray diffractometer. This is achieved by a method in which the orientation and position of the X-ray optics and the position of the X-ray source are measured relative to the base structure and are set at predefined target values, so that the X-ray radiation exiting from the X-ray source at the output end of the collimator and conditioned by passing through the X-ray optic is detectable with the set target values.

The present invention proposes that the adjustment of the primary side of an X-ray diffractometer, in particular a single crystal X-ray diffractometer, be facilitated by adjusting the position of the X-ray source and the position and orientation of the X-ray optics initially not iteratively on the basis of individual X-ray measurement steps relative to one another. Instead, a respective predefined setting relative to the base structure (also referred to as the base) on which these components are mounted is sought directly using those components. To this end, a measurement of the position of the X-ray source and the position and orientation of the X-ray optics relative to the base structure are performed, optionally even multiple times, and the components are adjusted until the achieving respective target values. A fitting relative orientation of the components among one another is then also achieved automatically.

Within the scope of the invention, no X-ray measurements on the diffractometer to be adjusted are necessary for the setting. The measurement of the position and/or orientation of the components relative to the base structure can take place fundamentally with the X-ray safety housing open within the scope of the invention, in particular mechanically or optically. The adjustment of the components can take place during the ongoing measurement of the position and/or orientation if desired. The setting of the target values can therefore take place very rapidly on the whole.

The measurement of the position and/or orientation of a component according to the invention (X-ray optics, X-ray source, optionally collimator and/or collimator aperture) relative to the base structure can take place directly with respect to the base structure or indirectly with respect to an auxiliary body designed in a defined (known) way and positioned in a defined (known) manner relative to the base structure. In the latter case the auxiliary body is preferably arranged and/or mounted on the base body only temporarily ("reference body"). This is then a temporary extension of the base structure.

As a rule, after setting the target values, at least 10% of the maximum beam intensity achievable with the X-ray diffractometer (after complete adjustment) is achieved already downstream from the collimator. The predefined target values can be determined experimentally once in advance for the type of diffractometer or they may also be calculated. After the predefined target values have been set, this is typically followed by precision adjustment steps to optimize the X-ray beam intensity and optionally the X-ray beam position.

A position within the scope of the invention will typically be measured in one direction (line focus systems, perpendicular to the line direction and to the beam propagation direction) or two directions (point focus systems) each of which runs perpendicular to the beam propagation direction (z). If desired, measurements may additionally be performed in the beam propagation direction (z). However, the components can usually be positioned with sufficient accuracy by means of stops in this direction (z). Within the scope of the invention, an orientation is typically measured along an axis (line focus systems, parallel to the line direction) or two axes (point focus systems) running perpendicular to the beam propagation direction (z).

The position and orientation of the X-ray optics may be adjusted within the scope of the invention by adjusting the X-ray optics within a housing or by adjusting the housing containing the X-ray optics or a combination of both. The position of the X-ray source is typically adjusted by adjusting the X-ray source (i.e., the X-ray source component, for example, an X-ray tube) including any housing (typically carrying a cooling system and/or a shutter), but as a rule the X-ray source is arranged in a stationary position in the housing. Alternatively, it is also possible to adjust the X-ray source within its housing, but as a rule the housing is arranged in a stationary position on the base structure. Here again, a combination of adjustment of the housing on the base structure and the X-ray source in the housing is conceivable.

The components (X-ray optics, X-ray source and preferably also the collimator) are advantageously mounted individually (independently of one another) and reversibly on the base structure. When one of the components (in particular the X-ray tube) is replaced, the other component(s) (in particular the X-ray optics) need not also be changed then. This facilitates the readjustment on reinstallation of the replaced component. It is usually sufficient in reinstallation for the replaced component to seek out the last position and/or orientation before this exchange again, possibly followed by a precision adjustment of only this component.

In a preferred variant of the method according to the invention, the orientation of the X-ray optic is measured with an accuracy of 1 mrad or better, and the positions of the X-ray optics and the X-ray source are measured and set with an accuracy of 50 μm or better, preferably 20 μm or better. Therefore, extensive adjustment of the X-ray diffractometer can still be performed even without an X-ray beam. The accuracies indicated are suitable in particular for the case when the X-ray optic is designed with a Montel mirror and the X-ray source is designed with a microfocus source. If the position of the collimator is also measured and set at a predefined target value, then this is also preferably measured and set with an accuracy of 50 μm or better, in particular 20 μm or better.

Particularly preferred is a variant, in which the orientation and position of the X-ray optics relative to the base structure and the position of the X-ray source relative to the base structure are set independently of one another. This prevents additive setting errors with the two components, and the predefined target values can be set particularly rapidly and in any order.

A variant in which the position of the X-ray source and the position and orientation of the X-ray optics are also measured by distance measurements is also advantageous. Distance measurements are relatively simple to perform. The distance measurements may be performed, for example, by mechanical scanning or by laser distance measurement. If the position of the collimator is measured, this is preferably also done by means of distance measurements.

In a preferred variant of the method, it is provided that the position and orientation of the X-ray optics are adjusted by adjusting the position and orientation of a housing of the X-ray optics in which the X-ray optic is arranged in a known position and orientation, in particular being fixedly arranged, and by measuring the position and orientation of the housing of the X-ray optics to determine the position and orientation of the X-ray optics. The X-ray optic is protected by the housing, in particular mechanically, and a reaction with atmospheric oxygen can be prevented by means of a vacuum or an He atmosphere in the housing. A vacuum or an He atmosphere also prevents absorption of air of the X-ray radiation so that the performance of the diffractometer is improved. The measurement of the housing is comparatively simple to perform from the outside; then the position of the X-ray optics can be determined relative to the base structure (calculated) by means of the known relative position of the X-ray optics in the housing. For this variant, the position and orientation of the X-ray optics relative to the housing are determined and/or adjusted in advance, for example, by means of a suitable measurement or a sufficiently precise manufacturing method.

In another advantageous variant of the method it is provided that the X-ray optic is arranged in a housing manufactured at least partially of optically transparent material, and the measurement of the position and orientation of the X-ray optics are performed through the optically transparent material, in particular by means of a laser distance measurement, in particular wherein the position and orientation of the X-ray optics in the housing of the X-ray optics are adjusted. The X-ray optic is protected in particular mechanically by the housing and a reaction with atmospheric oxygen can be prevented by a vacuum or an He atmosphere in the housing. A vacuum or an He atmosphere also prevent absorption of air of the X-ray radiation so that the performance of the diffractometer is improved. Direct measurement of the X-ray optics through the housing is particularly precise and does not require in particular any conversion from a housing position to an X-ray optics position. Adjustment of the X-ray optics in the housing can be detected and taken into account. Alternatively or additionally, an adjustment of the position and orientation of the X-ray optics via the housing of the X-ray optics may also be provided.

A variant of the method, which provides that the position of the X-ray source is adjusted in two linearly independent directions (x, y) perpendicular to the direction of beam propagation (z) relative to the base structure is also preferred, in particular, wherein the position of the X-ray source is measured by means of two distance measurements, and the position of the X-ray optic is adjusted in two linearly independent directions (x, y) perpendicular to the direction of beam propagation (z), and the orientation of the X-ray optics with respect to two axes (A, B) perpendicular to the direction of beam propagation (z) is adjusted relative to the base structure, in particular wherein the position and orientation of the X-ray optics are measured by means of four distance measurements. This procedure has also proven successful in practice in particular for point focus sources. The distance measurements are particularly simple to perform.

In one variant, the position of at least one collimator aperture of the collimator is measured relative to the base structure and is set at a predefined target value, so that with the target values set, X-ray radiation exiting from the X-ray source at the output end of the collimator and conditioned by the X-ray optic can be detected. By including an adjustable collimator in the measurement and setting of the components at target values according to the invention, an initial faulty positioning of the collimator and/or the at least one collimator aperture can be prevented and/or minimized, so that the adjustment of the primary side can take place more quickly on the whole. The collimator may in the simplest case be designed with only one collimator aperture ("1-hole aperture collimator"), which is then measured and set at a target value, for example, by means of the beam tube of the collimator. It is likewise possible to use a collimator having two collimator apertures ("2-hole aperture collimator"). In this case, for example, a collimator aperture can be measured and set at a target value, for example, via the beam tube and the other collimator aperture may be only adjustable (but not measurable) wherein the other collimator aperture is usually set at an approximately central position at the start. However, it is also possible to measure both collimator apertures and to set them at target values. The latter case also corresponds to a measurement and setting of the position and/or orientation of a collimator component having two collimator apertures arranged fixedly thereon. As an alternative to this variant it is also possible to use a collimator that is not adjustable, and in particular is arranged fixedly preferably wherein the collimator is arranged directly on the base structure.

The position of the at least one collimator aperture of a collimator relative to the base structure is advantageously set independently of the position of the X-ray source and the position and orientation of the X-ray optics. This in turn prevents setting errors from being additive and makes it possible to set the predefined target values particularly rapidly and in any order.

In an advantageous variant of the method, it is provided that after setting the predefined target values, a precision adjustment of the position of the X-ray source is carried out in which the beam intensity on the output side of the X-ray optic is maximized, in particular wherein the collimator is removed from the beam path of the X-ray diffractometer for this precision adjustment of the position of the X-ray source. This iterative precision adjustment with the X-ray beam is particularly simple because it relates only to one or two adjustment parameters. With this in particular, deviations in the source focus position (in the X-ray source component, for example, in the X-ray tube) from the ideal position caused by tolerance in components can be compensated.

In a particularly preferred method variant, after setting the predefined target values and optional precision adjustment of the position of the X-ray source, a joint precision setting of the position of the X-ray source and the position of the X-ray optic is performed in which the beam intensity is maximized at the output end of the collimator, wherein the X-ray optics and the X-ray source are each moved by the same distances in the same directions between intensity measurements. This iterative joint precision adjustment of the X-ray beam is also particularly simple because it effectively relates only to one or two degrees of freedom. With this precision adjustment, errors in the beam position relative to the collimator due to component tolerances in particular can be compensated in this way. After the joint precision adjustment, a(n) (additional) precision adjustment of the position of the X-ray source for maximization of intensity downstream from the collimator may then be performed in which the beam position at the output end of the X-ray optic is not altered further. For the joint precision adjustment, the collimator can be removed from the beam path of the X-ray diffractometer, in particular wherein a calibrated 2D detector is moved into the beam path instead of the collimator and the X-ray beam is adjusted to a target position on the 2D detector which corresponds to the position of the collimator aperture. Due to the use of the 2D detector, the beam intensity at the output end of the collimator can be maximized as a result.

In another advantageous method variant, after setting the predefined target values and optional precision adjustment of the position of the X-ray source, there is a precision adjustment of the position of at least one collimator aperture of the collimator, in which the beam intensity at the output end of the collimator is maximized. This iterative precision adjustment with the X-ray beam is especially simple because (depending on the collimator aperture) it relates to only one or two adjustment parameters. With this precision adjustment, in particular deviations in the position of the collimator aperture of the collimator from the ideal position and/or relative to the beam position, caused by component tolerances in particular can be compensated. In this variant there usually need not be any subsequent maximization of X-ray intensity through precision adjustment of the position of the X-ray source.

A preferred method variant provides that, before adjusting the predefined target values, first a position of a source focus of the X-ray source is determined relative to a housing of the X-ray source or the adjustment is made to a predefined focus target value relative to the housing and the position of the X-ray source is adjusted by adjusting the position of the housing of the X-ray source, and for determining the position of the X-ray source, the position of the housing of the X-ray source is measured. Through this procedure, errors due to an inaccurate position of the source focus in the X-ray source (in the X-ray source component, for example, the X-ray tube) can be compensated. The position of the source focus relative to the housing is preferably determined with an accuracy of 50 µm or better, especially preferably 20 µm or better, or is adjusted to the focus target value. This is preferably done before the X-ray source is arranged on the diffractometer, for example, while it is still at the X-ray manufacturer's plant. Alternatively, the position of the source focus can also be determined relative to the base structure and can be set at a focus target value relative to the base structure by moving the X-ray source, in particular in the housing.

A method variant which provides that after complete adjustment of the primary side, the orientation and position of the X-ray optics and the position of the X-ray source and optionally also the position of the at least one collimator aperture of the collimator relative to the base structure are optionally measured again and the respective measured data are recorded, and after a misalignment of one or more components, in particular due to an earthquake or some other external vibration of the X-ray diffractometer, the components are adjusted relative to the base structure in accordance with the recorded measured data. Due to this procedure, an X-ray diffractometer can be quickly readied for operation again in particular after an unintentional misalignment.

Preferred is also a method variant in which the primary side as a whole is aligned with the sample by moving or pivoting the base structure with respect to a foot element that is connected to a goniometer, in particular wherein the foot element is rigidly connected with the goniometer, and in particular wherein the sample is arranged on the goniometer. The base structure can typically be moved or pivoted by means of adjusting elements, in particular adjusting screws, on carriers with respect to the foot element.

Also within the scope of the present invention is an X-ray diffractometer, wherein a primary side of the X-ray diffractometer comprises a collimator, an X-ray optic and an X-ray source, in particular an X-ray tube, wherein the collimator, the X-ray optic and the X-ray source are mounted directly or indirectly on a base structure, and wherein the orientation and position of the X-ray optic and the position of the X-ray source relative to the base structure can be adjusted by adjustment devices, characterized in that the X-ray diffractometer comprises one or more measurement devices with which the orientation and position of the X-ray optics and the position of the X-ray source can be determined relative to the base structure. With the measurement device(s), the X-ray optic and the X-ray source can be positioned (adjusted) so accurately that an X-ray intensity sufficient for an additional precision adjustment can already be detected downstream from the collimator. For the adjustment of the components by means of the measurement device(s), no X-ray beam is necessary. The measurement device(s) preferably operate mechanically or optically. The X-ray diffractometer may comprise a plurality of measurement devices arranged fixedly for simultaneous detection of all position and orientation information. Alternatively, the X-ray diffractometer may comprise only one measurement device which may be arranged at different measurement sites so that all position and orientation information can be detected sequentially in time. Likewise, a mixture of fixedly arranged measurement devices and those that can be arranged at different measurement sites is also possible. The adjustment devices are typically adjusting screws.

In a preferred embodiment of the X-ray diffractometer according to the invention, the one or more measurement devices have a measurement accuracy of 1 mrad or better for the orientation of the X-ray optics and have a measurement accuracy for the position of the X-ray optics and the X-ray source of 50 μm or better, preferably 20 μm or better. Therefore, an extensive adjustment of the X-ray diffractometer may still take place even without the X-ray beam. The stated accuracies are suitable in particular for the case when the X-ray optic is designed with a Montel mirror and the X-ray source is designed with a microfocus source.

A preferred embodiment provides that the one or more measurement devices comprise a mechanical scanning element and/or a laser distance measurement element. These types of measurement device are reliable and easy to handle. In addition, the one or more measurement devices may comprise an inductive distance measurement element or a capacitive distance measurement element.

Also preferred is an embodiment in which the X-ray optic is designed with a Montel mirror or a Goebel mirror. With these X-ray optics, beam conditioning in up to two dimensions is easily possible. Coating errors (deviation in the multi-layer period from the ideal value) are preferably 3% or less, preferably 1% or less, especially preferably 0.2% or less. In corresponding coating errors, a resulting angle error of the reflected X-ray beam remains on the order of magnitude of the typical reflex width (or less). In addition, form errors are preferably 20 angular seconds r.m.s. or less, preferably 10 angular seconds r.m.s. or less, especially preferably 1 angular second r.m.s. or less. With corresponding form errors (tangent errors) there remains a form error contribution of the position of the sample focus that is smaller by a factor of approximately 5 (or more) than the sample diameter under typical conditions. A polycapillary optic is also possible as the X-ray optics.

In one embodiment, the X-ray source is advantageously designed with a microfocus X-ray tube, in particular a stationary microfocus X-ray tube, a rotary anode X-ray tube or a liquid metal X-ray tube. These types of X-ray sources can be preadjusted within the scope of the invention by the measurement device(s) with respect to the base structure.

The microfocus X-ray tube is typically designed with an optical source focus diameter of 50 μm or less.

An embodiment in which one or more measurement devices are arranged on a single one-piece component and/or all the measurement sites for one or more measurement devices are designed on the single one-piece component is especially preferred. This avoids additive errors relative to one another in the adjustment of the positions and orientations of the components.

An embodiment in which it is provided that the X-ray diffractometer comprises a reference body is also advantageous, wherein the reference body is mounted reversibly on the base structure, and the one or more measurement devices are arranged on the reference body and/or all the measurement sites for the one or more measurement devices are designed on the reference body. The reference body may be used in a targeted manner during the adjustment of the primary side of the reference diffractometer and removed again for the ongoing measurement operation. In this way, the X-ray diffractometer can be kept compact in ongoing measurement operation. Addition of errors in setting the positions and orientations of the components relative to one another can be prevented by the arrangement of the measurement device(s) and/or measurement sites on the reference body. The mounting of the reference body should be reproducible to an accuracy of 50 μm or better in the directions to be adjusted. The reference body is preferably designed as a single one-piece component (see above).

A preferred refinement of this embodiment provides that the reference body can be locked on a guide running in the direction of beam propagation (z), in particular a groove can be pushed onto the base structure and can be locked on the base structure, in particular by means of adjusting screws, and a stop element, in particular on the reference body or on the base structure or on a housing of the X-ray optics or on a holding device of the X-ray optic is provided, with which a defined position of the reference body on the guide can be sought. By means of the guide, the reference body can be positioned easily and precisely on the base structure perpendicular to the beam propagation direction (i.e., with respect to x, y) (preferably with an accuracy of 50 μm or better, especially preferably 20 μm or better), so that the measurement of the components from the reference body outward can be used to measure the positions and orientations relative to the base structure. The positioning of the reference body in the z direction with the stop element is generally sufficiently accurate for the conditioning of the X-ray beam. The stop may be provided in particular on an intermediate element of the holding device.

A further development of this refinement provides that the X-ray optic is mounted on the base structure by means of a holding device. A base element of the holding device can be moved along a base guide, in particular a groove, running in the direction of beam propagation (z) of the base structure and can be locked on the base structure, in particular wherein an end stop and/or a scale for the base element is formed. An intermediate element of the holding device is adjustable with respect to the base element in two mutually perpendicular directions (x, y) which are perpendicular to the direction of beam propagation (z), hereinafter referred to as the first direction (x) and the second direction (y). The X-ray optic is tiltable with respect to the intermediate element about two mutually perpendicular axes (A, B) which run perpendicular to the direction of beam propagation (z). The X-ray optic is encompassed by the intermediate element, and the stop element of the reference body can be moved along the first direction (x) toward the intermediate element, wherein the intermediate element and the stop element form mutual stop faces parallel to the first and second directions (x, y). This construction makes available the degrees of freedom required for the positioning and orientation of the X-ray optics in a simple manner. The stop element can be placed on the holding device, in particular the intermediate element, to align the reference body. By retracting the extractable stop element after the z direction of the reference body, a transfer of force to the holding device can be prevented by tightening the adjustment screws or the like in securing the reference body.

In an advantageous embodiment of the X-ray diffractometer according to the invention, the X-ray diffractometer has a foot element wherein a position and/or orientation of the base structure with respect to the foot element is adjustable, in particular wherein the orientation of the base structure is adjustable along two mutually perpendicular axes running perpendicular to the beam propagation direction (z). The primary side and/or the X-ray beam can easily be aligned with the sample by means of the adjustability of the base structure with respect to the foot element. The foot element is typically rigidly connected to a goniometer of the X-ray diffractometer.

Especially preferred is an embodiment which provides that the collimator, the X-ray optics and the X-ray source independently of one another are mounted on the base structure and that separate adjusting devices are provided for the X-ray optics and the X-ray source, so that the orientation and position of the X-ray optics relative to the base structure and the position of the X-ray source relative to the base structure can be adjusted independently of one another. Typically the collimator also has a separate adjusting device for one or more collimator apertures (pinhole apertures) for independent adjustment of the respective position relative to the base structure. This structure prevents adjustment errors from becoming additive and the predefined target values can be adjusted especially rapidly and in any order.

An advantageous refinement of this embodiment provides that the X-ray optics and/or the X-ray source and/or the collimator is/are each reversibly mounted on an intermediate holder and each intermediate holder is adjustable with respect to the base structure by means of its own adjusting device, in particular wherein the intermediate holder or the intermediate holders are designed as clamping holders or magnetic holder, preferably three-point magnetic holders with a preset clamping force or holding force. By means of the intermediate holders it is possible to replace individual components (for example, the X-ray source if there is wear) without altering the position and orientation of the replaced component. The position and orientation of the replaced component are determined by the adjustment of the intermediate holder which can remain unchanged on the base structure during the replacement.

An embodiment in which the adjustment devices for adjusting the position of the X-ray source and for adjusting the position of the X-ray optics in a respective direction are designed as adjusting screws with the same pitch is also advantageous. It is therefore readily possible to adjust the position by an identical distance in a joint precision adjustment of the X-ray source and X-ray optics with both components. The adjusting screws involved in this on the two components are each adjusted by the same angle for this purpose.

Additional advantages of the invention are derived from the description and the drawing. Likewise, the features mentioned above and those listed further below according to the invention may each be used individually, either alone or several together in any combinations. The embodiments illustrated and described here are not to be understood as a final listing but instead have an exemplary character for the description of the invention.

BRIEF DESCRIPTION OF THE DRAWINGS

The invention is illustrated in the drawings and is explained in greater detail below on the basis of exemplary embodiments, in which.

DETAILED DESCRIPTION

Figure 1:
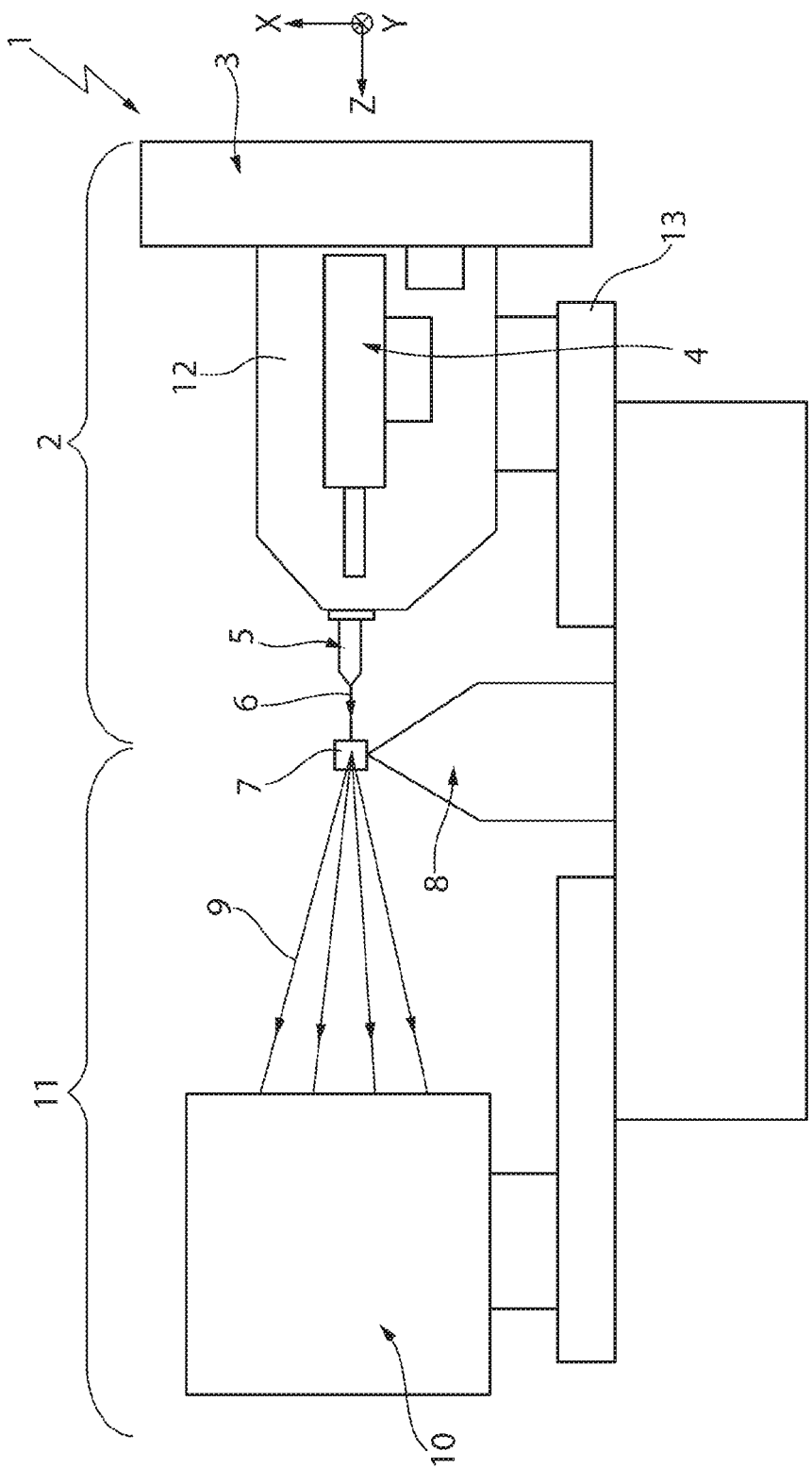
FIG. 1 shows a schematic overview of an embodiment of an X-ray diffractometer according to the invention.

With the present invention, the adjustment of the primary side of an X-ray diffractometer can be significantly improved and accelerated and made more user friendly.

The adjustment concept according to the invention makes use of the elliptical equation which theoretically defines the ideal position of the individual components. Consequently, it is proposed according to the invention that the source focus of the X-ray source be positioned with a great accuracy in the first focal point. The X-ray optics should also, following the elliptical equation, be positioned and/or aligned with a high precision so that the sample sits in the second focal point of the ellipsis (in the case of a parabola the second focus is in the infinite). If the long axis of the ellipsis is aligned so that it points at the detector at a right angle, then the entire system is ideally adjusted. Additional components such as the collimators are also to be mounted in their ideal target positions.

In recent years, there has been a steady further development in the field of X-ray optics to improve the X-ray intensity on the sample and/or to obtain better resolution of the X-ray diffraction diagrams.

Multi-layer mirrors can be manufactured with a coating error of only 0.2% over the entire mirror surface, so that the resulting angle error for Cu-K$\alpha$ X-ray radiation is only 0.001-0.004°, which is definitely smaller than the reflex width of 0.057° for Cu-K$\alpha$ radiation. The situation is similar for other types of radiation. The coatings may therefore be regarded as almost ideal.

The situation is similar for the shape errors: mirrors with shape errors <10 arc sec (standard deviation=root mean square, r.m.s.) can be achieved today in mass production. Assuming a local angle error of typically 5 arc sec=5/3600°=0.0014°=2.44E−5 rad for a mirror of high quality, this yields, here again, a value that can be regarded as almost ideal. If the mirror segment considered here should be 200 mm away from the sample focus, then the focus error contribution would be equal to 2.44E−5 rad*200 mm=5 $\mu$m, i.e., only insignificant in comparison with the ideal value of 100 $\mu$m.

In summary, it can thus be stated that the multi-layer X-ray mirrors today can be manufactured to be almost ideal. The inventors have recognized that, due to the high manufacturing quality of the X-ray optics, this creates the prerequisite for the inventive high-precision positioning and/or alignment of the X-ray optics according to the elliptical equation with geometrically determined target values (without turning on the X-ray beam), so that most of the previous adjustment steps can be eliminated or abbreviated.

In the wake of the invention, the question of to what extent one can approach this ideal system according to the elliptical equation with a real system has been addressed. Therefore, starting with a single crystal diffractometer according to the prior art described above, error propagation calculations were performed. One result of these calculations was that various components according to the prior art are so interconnected that the resulting, relatively long and poor tolerance chains and the resulting additive tolerances are far too high to arrive at the range of adjustment accuracy of a few 10 $\mu$m, which is necessarily the result when using source sizes of 35 $\mu$m or samples sizes of 100 $\mu$m. The beam path of the X-ray diffractometer on the primary side was therefore redesigned to yield the shortest possible tolerance chains. In the wake of the invention, preferably all primary-side components are mounted directly on a common base structure (also called base body). Indirect assemblies (via other components) are avoided.

Furthermore, in a preferred embodiment, it is proposed that a preferably single one-piece reference body with developed measurement sites, be reversibly mounted on the base structure, so that the target positions and/or target orientations of the primary-side components, i.e., the X-ray source, the X-ray optics and collimator (and/or its collimator aperture or collimator apertures) can be adjusted by means of the measurement sites directly by means of distance measurements with respect to the reference body. The reference body then lengthens the base structure for the measurement and adjustment of the components. The reference body together with the distance measurements, which are thereby made possible, shortens the tolerance chain of the components significantly and makes a purely mechanical preadjustment of the system without the X-ray beam possible in precisely such a way that, when the diffractometer is turned on, X-ray radiation that has already been conditioned by the X-ray optic is measurable at the output end of the collimator. Only minor correction adjustments are necessary to achieve a maximum photon flux at the output end of the collimator. Residual errors are thus compensated by means of suitable adjusting screws. In normal measurement operation, the reference body may be removed and does not interfere with this. It should be pointed out that, alternatively, instead of a reference body mounted reversibly on the base structure, the position and orientation of the components can be measured directly with respect to the base structure (and/or a fixed part thereof) and adjusted, likewise with the advantages of a short tolerance chain and a high precision mechanical preadjustment.

In contrast with the prior art, the primary side components are preset at their target positions and/or target orientations mechanically, i.e., without X-ray radiation. Therefore, the adjustment steps 1) to 3) described above in the prior art, i.e., setting the Montel optic at the source focus with subsequent maximization of intensity, adjustment of the position and/or orientation of the X-ray beam and of the collimator relative to one another, so that the X-ray radiation is visible at the output end of the collimator, and finally, maximization of intensity at the output end of the collimator can be greatly accelerated and made more user friendly. The number of individual adjustment steps described above is greatly reduced.

It is readily possible and intuitively feasible to change the beam position by simultaneously moving the X-ray optics and the X-ray source when the corresponding adjustment screws of the X-ray optics and X-ray source have the same thread pitch in one embodiment. Due to this innovation, there is also a greatly reduced probability of adjusting the source focus and the X-ray optics relative to one another to the extent that the X-ray mirror is no longer reflective, which would lead to a further time loss.

In addition, the quality of the X-ray optics as well as the positioning accuracy with respect to the target position and/or target orientation can be set so high that the X-ray beam conditioned by the X-ray mirror and passing through the collimator usually strikes the detector at a right angle. This makes it unnecessary to repeat the adjustment steps described in the prior art, so that a further acceleration of the adjustment of the primary side of an X-ray diffractometer is achieved.

Another advantage of the invention is that after complete adjustment of the diffractometer, the actual position and/or the actual orientation of the X-ray source, X-ray optics and collimator can be measured by means of distance measurements with respect to the reference body (or with respect to the base structure in general) and recorded. If the system has gone out of adjustment due to a variety of reasons, for example, due to moving the diffractometer, due to misalignment by an untrained user, due to earthquakes, etc., then the system can rapidly return to an adjusted state with the help of the reference body and the distance values recorded (and/or the base structure and the recorded position and orientation data in general). This has not previously been possible according to the prior art.

FIG. 1 shows a specific embodiment of an X-ray diffractometer 1 according to the invention, in particular a single-crystal X-ray diffractometer. The X-ray diffractometer 1 has a primary side (area of the primary beam path) 2, comprising an X-ray source 3 (preferably a point focus source with a focus size between 20 μm and 100 μm or with a focus size of 35 μm or less), an X-ray optics 4 and a collimator 5. The X-ray beam 6 generated with the primary side 2 propagates in the z direction and strikes a sample 7 which is arranged on a goniometer 8 and can be rotated with the latter; preferably the goniometer 8 is designed as a triple-axle goniometer. Diffracted X-ray radiation 9 emitted by the sample 7 is recorded by a two-dimensional detector 10. The X-ray radiation 9 emanating from the sample 7 and the detector 10 belong to the secondary side (area of the secondary beam path) 11 of the X-ray diffractometer 1.

The X-ray source 3, the X-ray optics 4 and the collimator 5 here are each mounted independently of one another on a base structure 12 and are adjustable independently of one another with respect to this in a manner to be described below. The base structure 12 is in turn adjustable with respect to a foot element 13 in a manner to be described below. The foot element 13 here is rigidly connected to the goniometer 8.

Figure 2:
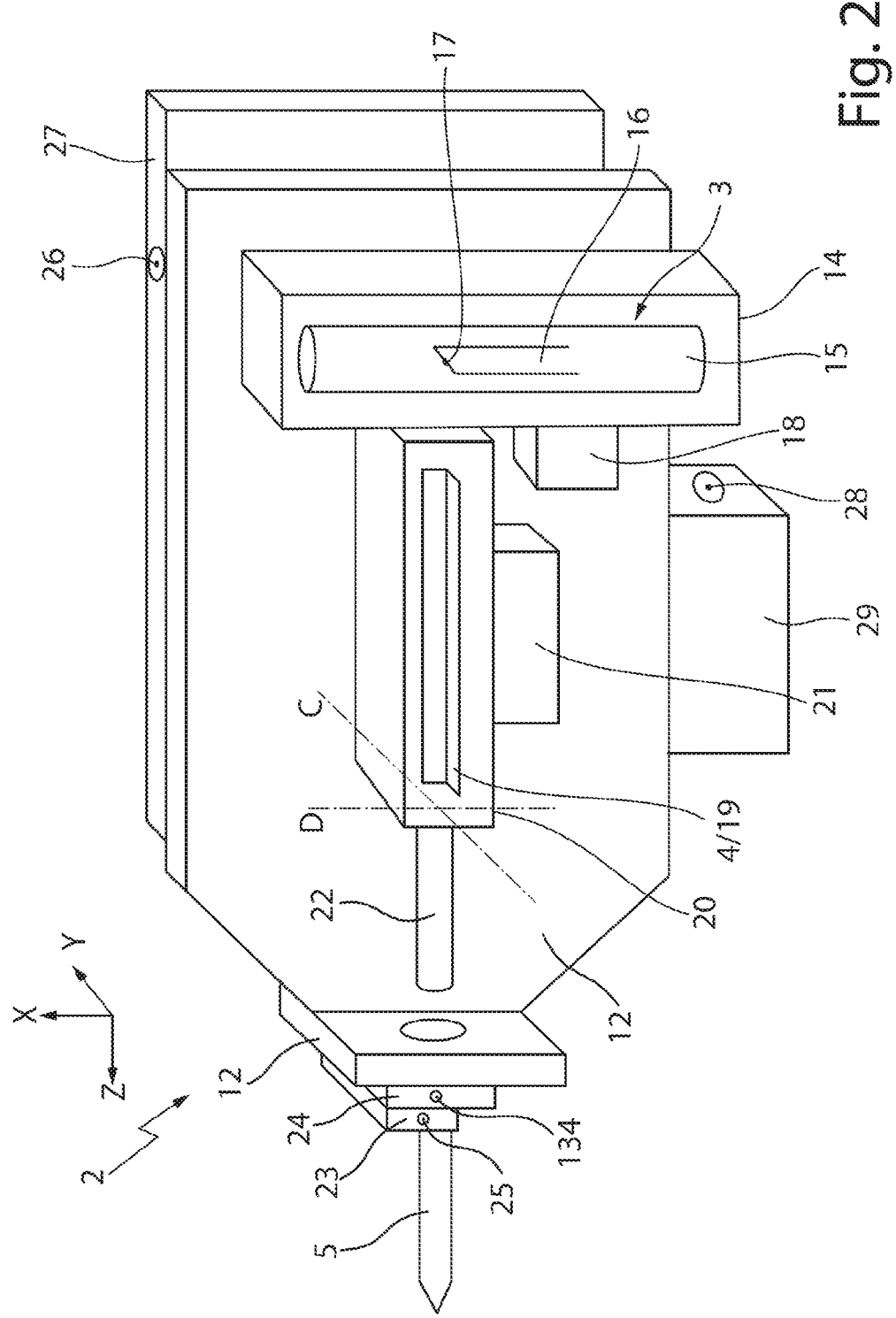
FIG. 2 shows a schematic oblique view of the primary side of the X-ray diffractometer.

FIG. 2 illustrates the primary side 2 of the X-ray diffractometer in greater detail. X-ray source 3 here is designed as an X-ray tube 15, which is arranged in a housing 14 of the X-ray source 3. An anode 16 which forms a source focus 17 at the location where accelerated electrons strike the anode 16 is arranged in the X-ray tube 15. The housing 14 and thus also the X-ray tube 15 are mounted on the base structure 12 with an adjustable mounting device 18. A shutter (not shown in detail) for blocking the X-ray beam (not shown) that is propagated essentially in the z direction is formed on the housing 14.

The X-ray optics 4 is formed here with a Montel mirror 19 comprising two gradient multi-layer mirrors arranged at a right angle, wherein the Montel mirror is arranged in a defined (known) manner in a housing 20 of the X-ray optics 4 so that the position and orientation of the X-ray optics 4 can be deduced from the position and orientation of the housing 20. The housing 20 and thus also the X-ray optics 4 are mounted on the base structure 12 by an adjustable holding device 21. Here again, a helium beam tube 22 is arranged with which atmospheric scattering and/or atmospheric absorption of the X-ray beam is/are minimized.

The collimator 5 which forms a (first) collimator aperture (pinhole aperture) at the tip of its beam tube in FIG. 2 at the front end at the left is equipped with a plate-shaped base element 23 with which the beam tube can be translated horizontally (in the y direction) and vertically (in the x direction) (cf. the adjusting the screw 25). The base element 23 is mounted on the base structure 12 by means of a holding element 24. If a two-hole aperture collimator is to be used as is the case here, then the holding element 24 also includes a second collimator aperture (second pinhole aperture) (concealed in FIG. 2) and adjusting elements (cf. adjusting screw 134) for a transition of the second pinhole aperture.

The base structure 12 can be pivoted with respect to the foot element (not shown) about an axis C (running parallel to the y direction) by means of an adjusting element (here an adjusting screw 26) on a carrier 27. In addition, the base structure 12 can also be pivoted about an axis D (running parallel to the x axis) by means of an adjusting element (here an adjusting screw 28) on a carrier 29. In an alternative design, the base structure 12 can be moved vertically (in the x direction) with respect to the foot element by means of the adjusting screw 26 and the base structure can be moved horizontally (in the y direction) by means of the adjusting screw 28.

Figure 3:
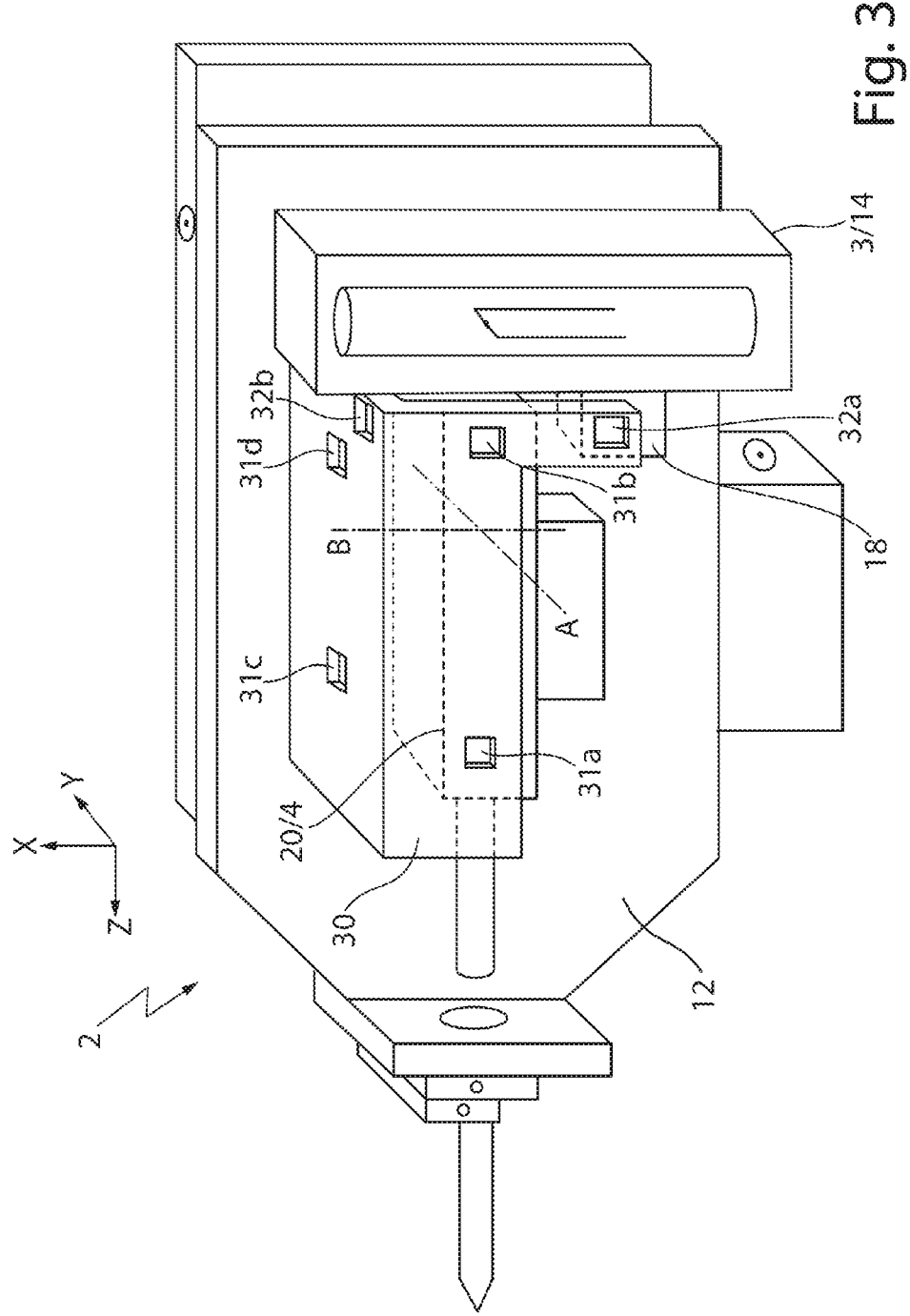
FIG. 3 shows a schematic oblique view of the primary side of the X-ray diffractometer, with the reference body for adjusting the X-ray optics and the X-ray source.

FIG. 3 shows the primary side 2 of FIG. 2, wherein now a reference body 30 is arranged on the base structure 12. The reference body 30 is mounted in a defined manner on the base structure 12 (reversibly), so that the position or orientation of these components with respect to the base structure 12 can be deduced via a determination of the position or orientation of components of the primary side 2 relative to the reference body 30.

Four measurement sites (apertures) 31a-31d are formed on the reference body 30 here. A depth gauge that is used (not shown) can use these measurement sites to determine the distance of a front side face and/or a top side of the housing 20 of the X-ray optics 40 from a front side face and/or a top side of the reference body 30 in a part on the left side and a part on the right side. These four items of distance information are enough to determine the position of the X-ray optics 4 (and/or its housing 20) with respect to the directions x and y and the orientation of the X-ray optics 4 and the orientation of the X-ray optics 4 with respect to the mutually orthogonal axes A (running parallel to the y direction) and B (running parallel to the x direction).

In addition, two measurement sites (apertures) 32a-32b are formed on the reference body 30, with which the depth gauge can determine distances of a (respective) part of the mounting device 18, on which the housing 14 of the X-ray source 3 is mounted in the known way (at least with respect to the relevant direction), from the reference body 30. The measurement sites 32a, 32b are in turn formed on the front side face and on the top side of the reference body 30 and permit a distance measurement from a front side face and a top side of said (respective) part of the mounting device 18. It is possible in this way to determine the position of the X-ray source 3 with respect to the directions x, y to the base structure 12.

Figure 4:
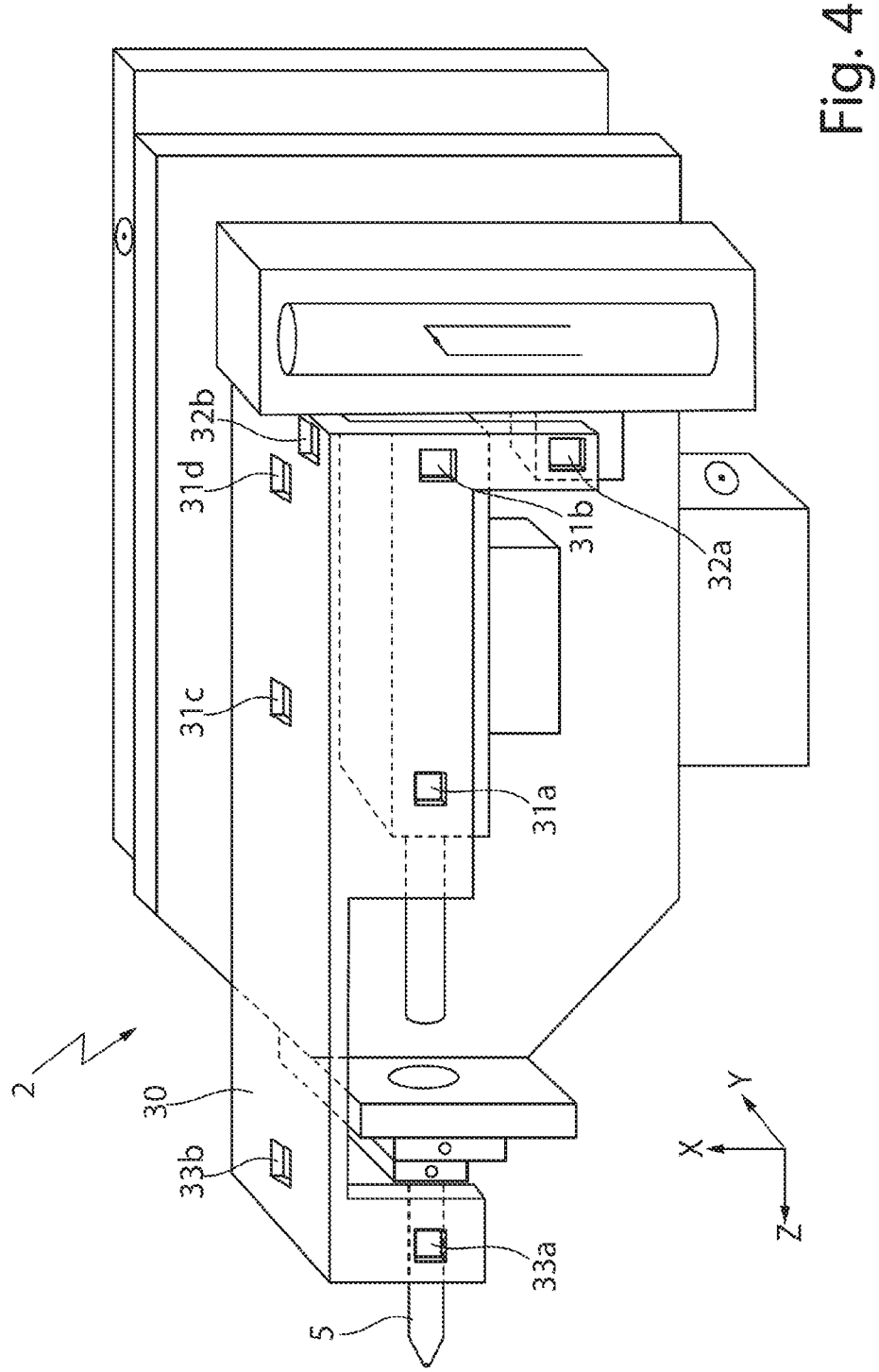
FIG. 4 shows a schematic oblique view of the primary side of the X-ray diffractometer, with an alternative reference body for adjusting the X-ray optics, X-ray source and collimator.

FIG. 4 illustrates a variant of the reference body 30 in which this also reaches around the collimator 5. With the measurement sites (apertures) 33a, 33b on the front lateral face and on the top side face of reference body 30, a depth gauge can also determine the distance in the x direction and y direction relative to the position of the collimator aperture on the tip of the beam tube of the collimator 5 (shown at the left side of FIG. 4).

It should be pointed out that in the two variants of FIG. 3 and FIG. 4, all the measurement sites 31a-31d, 32a-32b, 33a-33b are formed on the same one-piece component, namely the reference body 30.

Figure 5:
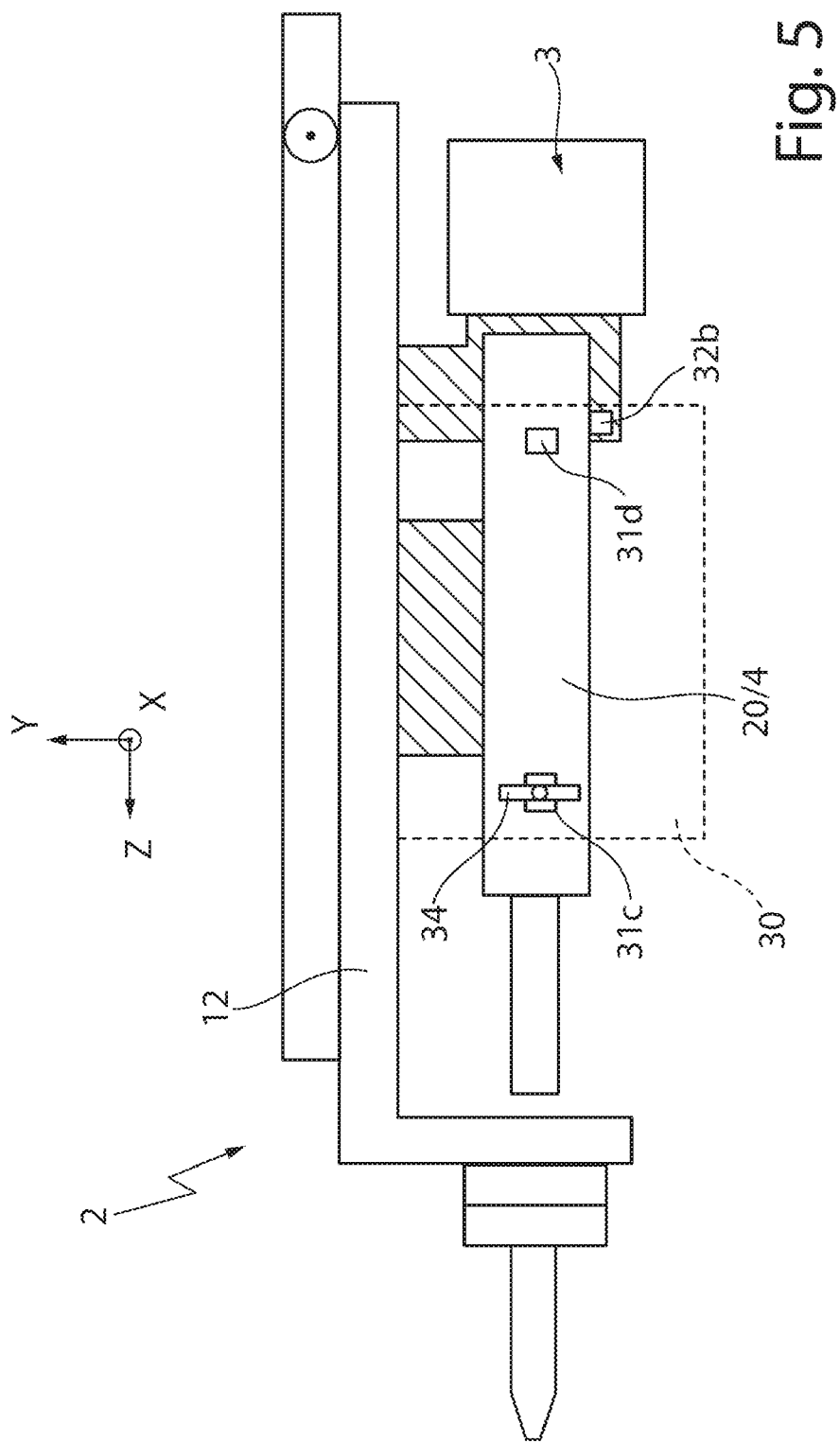
FIG. 5 shows a schematic view of the primary side of the X-ray diffractometer of FIG. 3.

FIG. 5 shows a view of the primary side 2 as shown in FIG. 3, wherein the reference body 30 is shown as transparent with dotted line contours. A mechanical scanning element (depth gauge) 34 has been inserted into the measurement site 31c here and can be used to measure the distance in the x direction (perpendicular to the plane of the drawing) of the reference body 30 relative to the housing 20 of the X-ray optics 4. The depth gauge has a measurement accuracy of approximately 10 μm.

Figure 6:
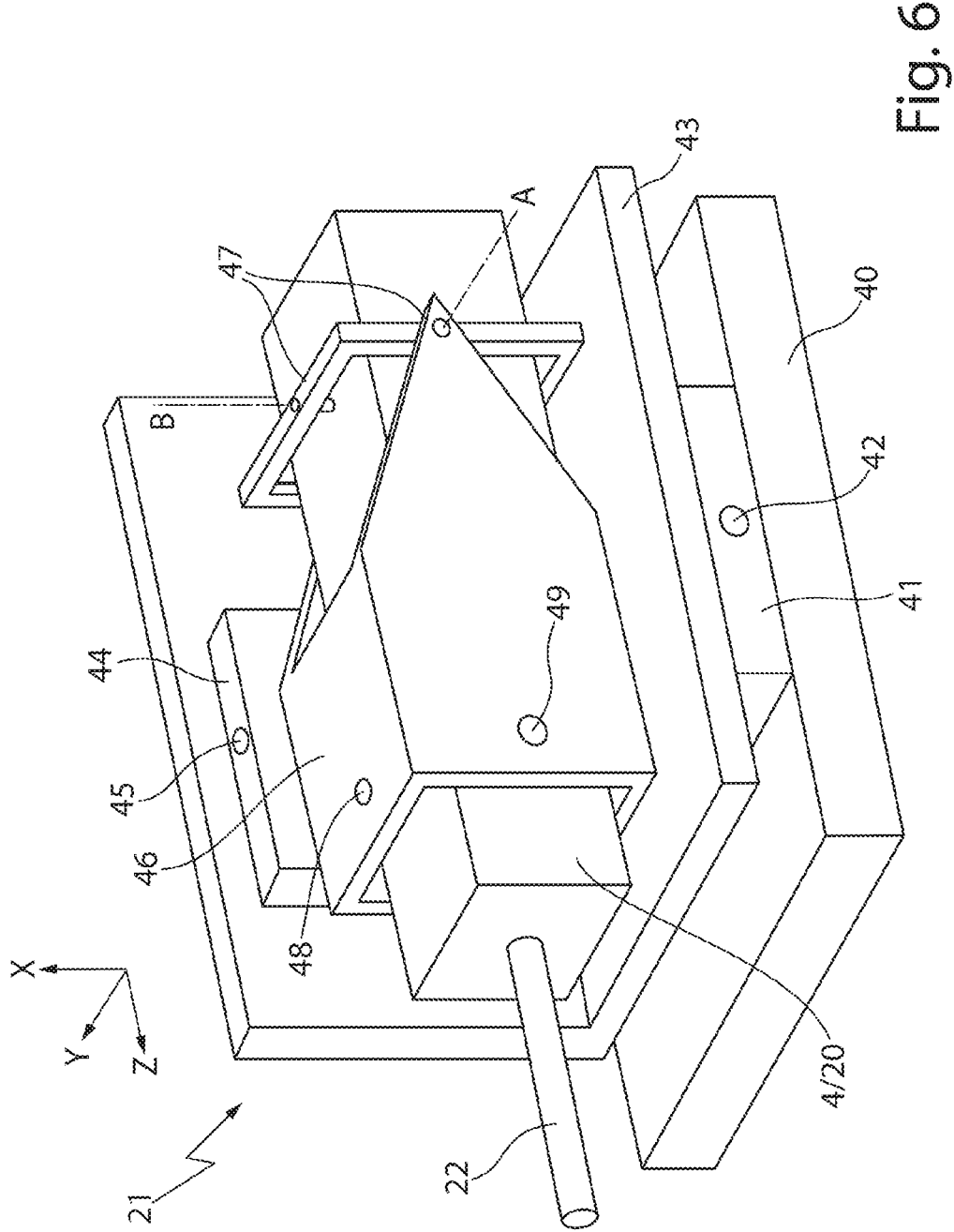
FIG. 6 shows a schematic oblique view of a holding device for the X-ray optics of the X-ray diffractometer.
Figure 7:
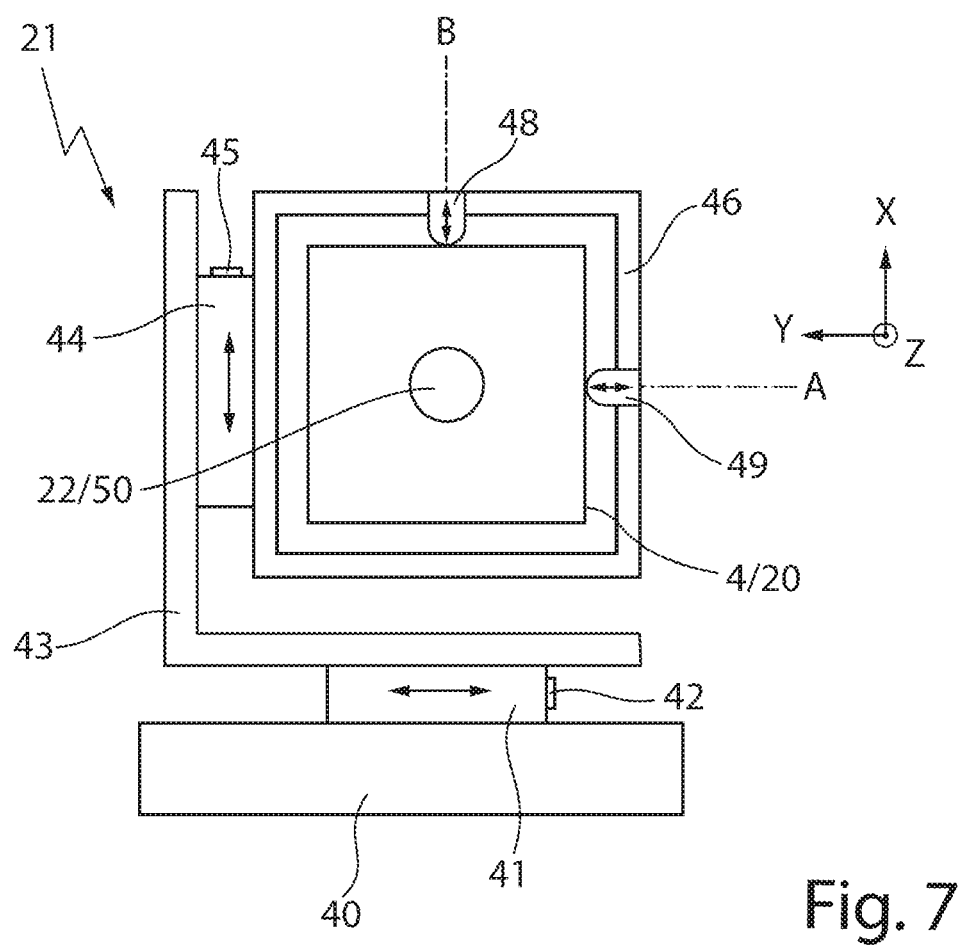
FIG. 7 shows a schematic frontal view of the holding device of FIG. 6.

The oblique view in FIG. 6 and the frontal view in FIG. 7 illustrate the mounting and adjustment of the X-ray optics 4 on the base structure by means of the holding device 21 in greater detail.

The holding device 21 has a base element 40 which is mounted on the base structure (also not shown) via a sub-base element (not shown) of the holding device 21, approximately with pins in a groove and fixation screws (cf. FIG. 12 in this regard) on the back side.

A carrier 43 having an L-shaped cross section can be translated horizontally (in y direction) with respect to the base element 40 by means of an adjusting device 41 with an adjusting screw 42. Again an intermediate element 46 can be translated vertically (in x direction) with respect to the carrier 43 by means of an adjusting device 44 with an adjusting screw 45.

The X-ray optics 4 is again mounted in the intermediate element 46. The intermediate element 46 reaches around the X-ray optics 4 in doing so. The X-ray optics 4 and/or its housing 20 (including the attached He beam tube 22) can be pivoted about the horizontal axis A and the vertical axis B in the intermediate element 46. For this purpose, a gimbal suspension 47 is set up on the intermediate element 46. Tilting about the axis A is adjusted by means of an adjusting device (adjusting screw here) 48 and the tilting about the axis B is set with an adjusting device (adjusting screw here) 49. The adjusting screws 48, 49 are guided in threaded holes in the intermediate element 46 and are supported on the housing 20 of the X-ray optics 4 at the end.

Figure 8:
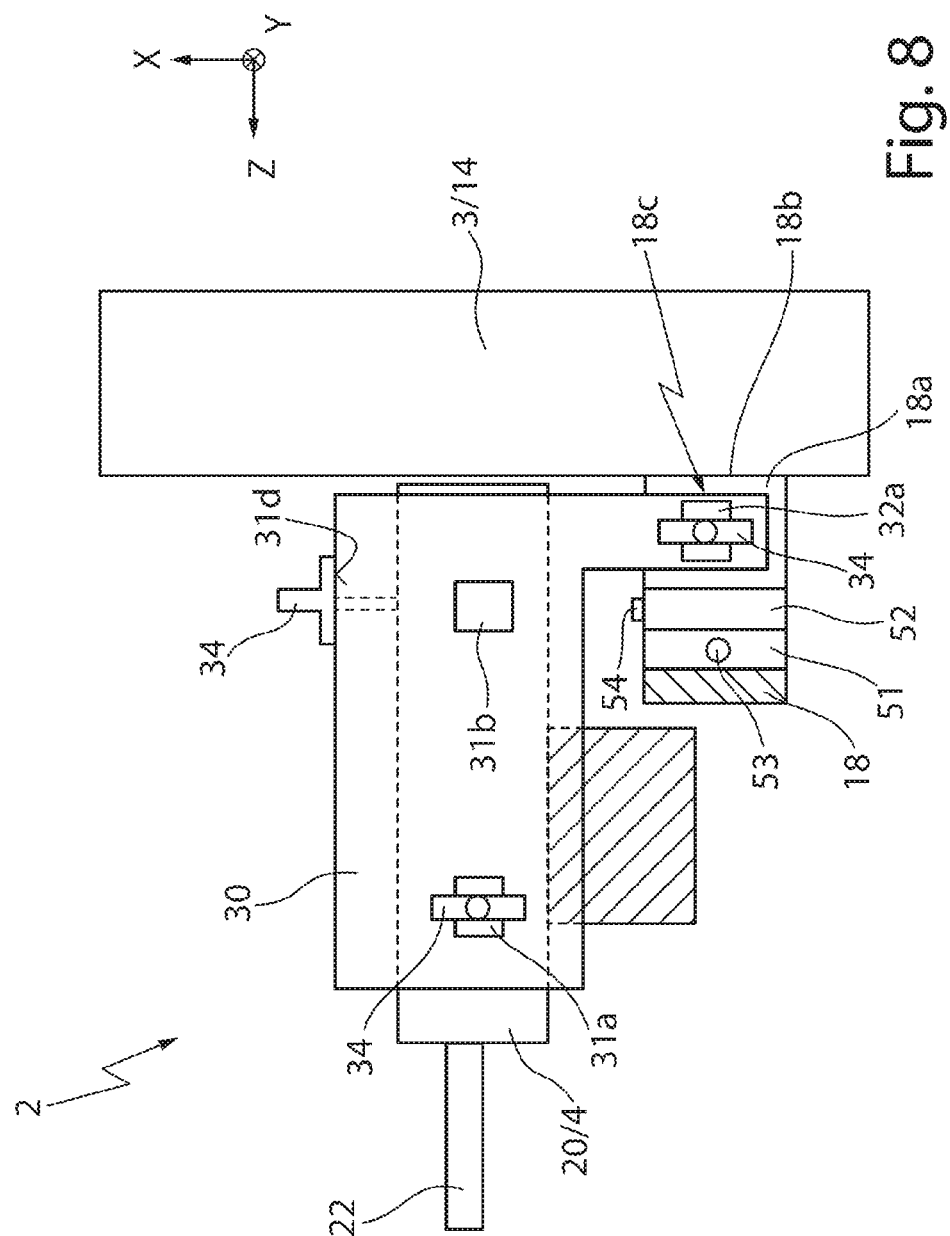
FIG. 8 shows a schematic side view of parts of the primary side of the X-ray diffractometer from FIG. 3 with multiple depth gauges on the reference body.

FIG. 8 shows a side view of the primary side 2 of FIG. 3. Three mechanical scanning elements (depth gauges) 34 are used here as measurement devices at the measurement sites, namely at the measurement sites 31a, 31d and 32a on the reference body 30.

With the scanning element 34 a portion of the mounting device 18, namely an intermediate holder 18a is contacted at the measurement site 32a. The intermediate holder 18a is connected to the X-ray tube 3 and/or its housing 14 at a joint 18b in a known reversible manner, namely with a snap-lock 18c here (cf. in this regard also FIGS. 13a-13c). Alternatively, a so-called quick-lock connection would also be possible. FIG. 8 also shows the adjusting device 51 for a horizontal (y) adjustment and the adjusting device 52 for a vertical (x) adjustment of the intermediate holder 18a and thus also of the X-ray source 3 by means of the adjusting screws 53, 54. When the X-ray tube 3 is replaced the intermediate holder 18a can remain in the adjusted position.

At the measurement site 31d, the mechanical scanning element 34 protrudes with a mandrel to the top side of the housing 20 of the X-ray optics 4. The distance from the measurement site 31d is obtained from the extension path of the mandrel.

Figure 9:
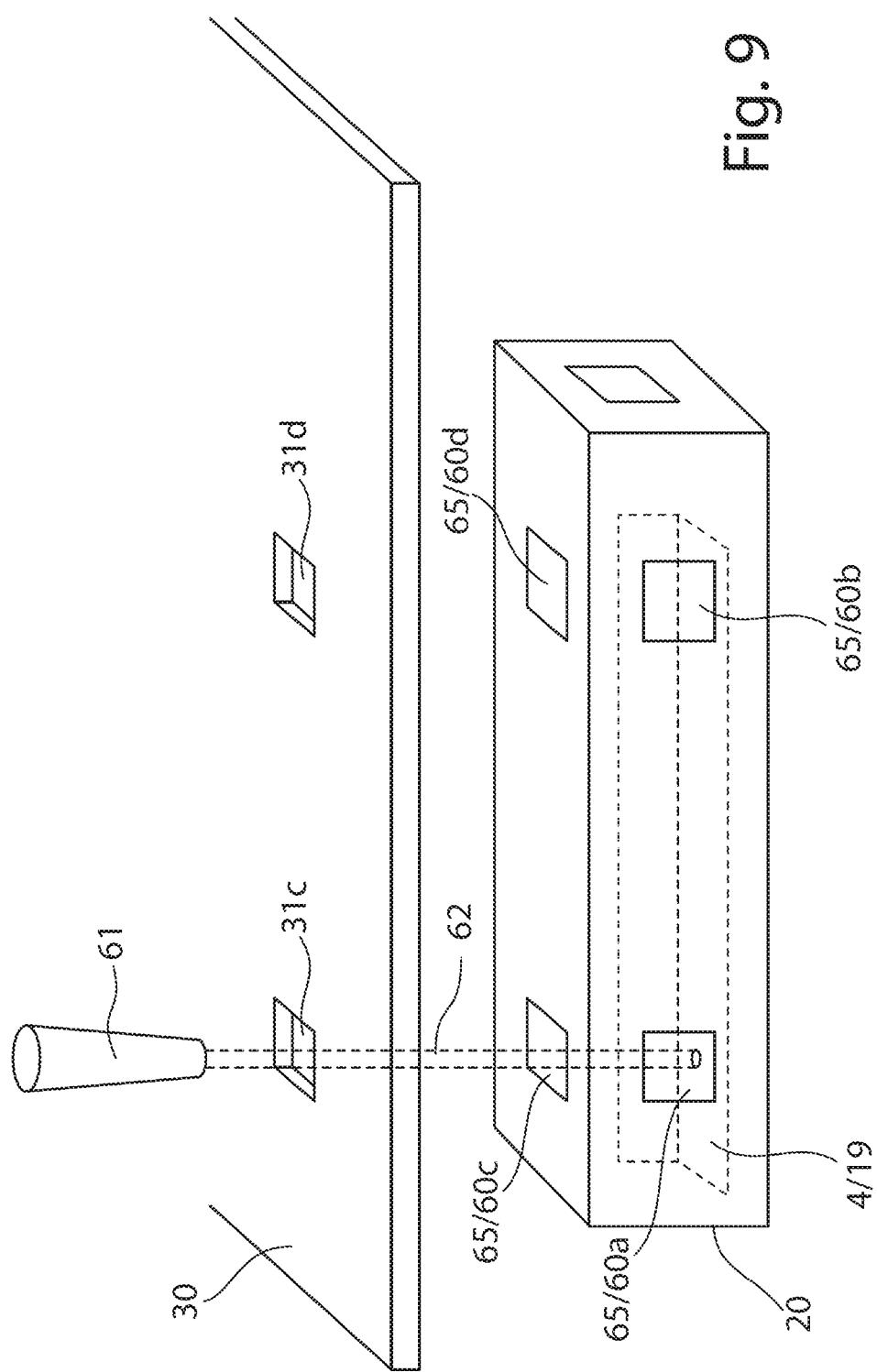
FIG. 9 shows a schematic oblique view of parts of the primary side of X-ray diffractometer, with an alternative laser distance measurement into an X-ray optics housing.

FIG. 9 illustrates an alternative variant for determining the position and the orientation of X-ray optics 4. The X-ray optics 4 is arranged in a housing 20, which has multiple windows 60a-60d, which are transparent for visible light (but are opaque for X-ray radiation). The windows 60a-60d are designed with an optically transparent material 65, which is impermeable for the X-ray radiation (attenuation preferably by at least a factor of 1000 with Cu-Kα), for example, lead glass.

With a laser distance measuring element 61, which is anchored in the measurement site 31c in a manner not shown in greater detail here (and positioned in a defined manner accordingly), a laser beam 62 is directed from the measurement site 31c in the reference body 30, into the interior of the housing 20 at the actual X-ray optics 4, which is a Montel mirror 19 here. For example, it is then possible to deduce the distance of the X-ray optics 4 to the measurement site 31c from the transit time of the laser beam 62 back to the laser distance measuring element 61.

The distance of the X-ray optics 4 with respect to other measurements sites (cf. 31d and also 31a, 31b cf. FIG. 3) can be determined with the other windows 60d, 60a, 60b with respect to the reference body 30 accordingly. In this variant, the X-ray optics 4 can also be adjusted in the interior of the housing 20.

Figure 10:
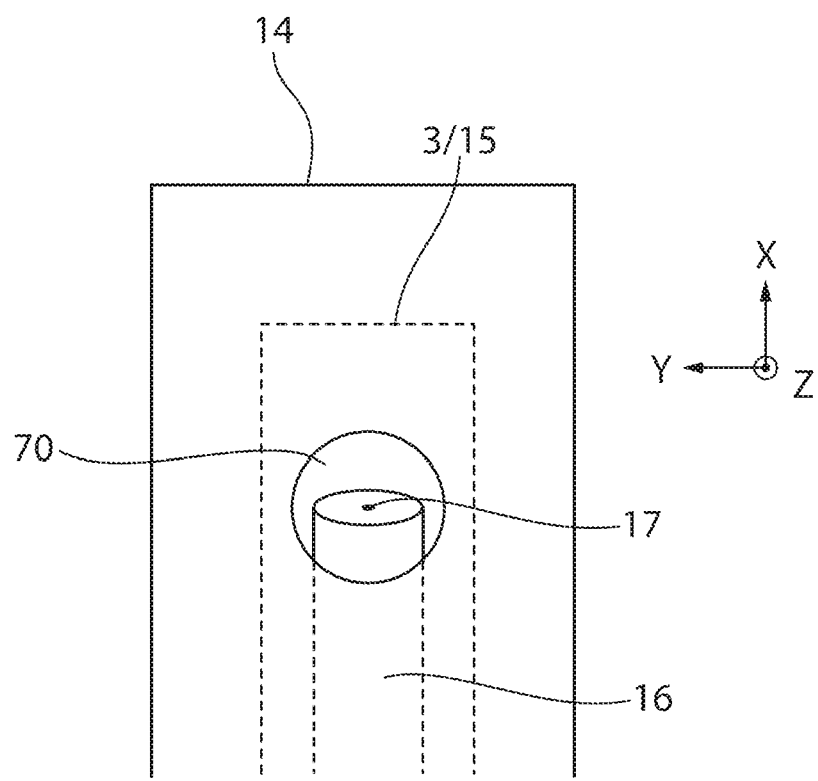
FIG. 10 shows a schematic sectional view of an X-ray source in a housing for the invention.

FIG. 10 shows a frontal view of the X-ray source 3 from FIG. 1. The X-ray source 3, here an X-ray tube 15, is arranged in the housing 14. The source focus 17 on the anode 16 sits behind a shutter aperture 70, which can be blocked as needed with a radiopaque cover ("shutter" not shown). For the invention, the source focus 17 is arranged at a defined position inside the housing 14, so that the source focus 17 can be placed in the desired manner by means of suitable positioning of the housing 14. In many cases, the manufacturer of the X-ray source 3 can place the X-ray tube 15 and the source focus 17 in the housing 14 with sufficient accuracy, so that in the adjustment of an X-ray diffractometer within the scope of the invention, the manufacturer's placement information can be used directly.

It is otherwise also possible to determine the position of the source focus 17 relative to the housing 14 in a preliminary experiment for calibration purposes, for example, relative to orientation point in the housing to thereby determine an offset (correction value or correction values) for the positioning of the housing 14 on the base structure. In another variant the position of the X-ray tube 15—and also the position of the source focus 17 in the housing 14 is adjustable (in at least one direction, namely along the tube axis corresponding to the x direction here) and is set at a desired position in a preliminary experiment (assumed for further positioning of the X-ray source 3) relative to the housing 14 ("focus target value") and secured there.

Figure 11A:
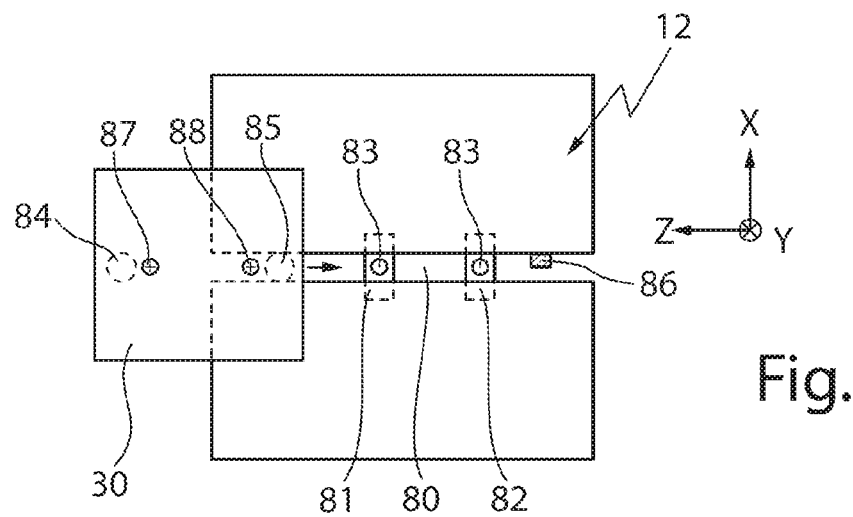
FIG. 11a shows a schematic side view of parts of the base structure of the X-ray diffractometer before mounting of the reference body.
Figure 11B:
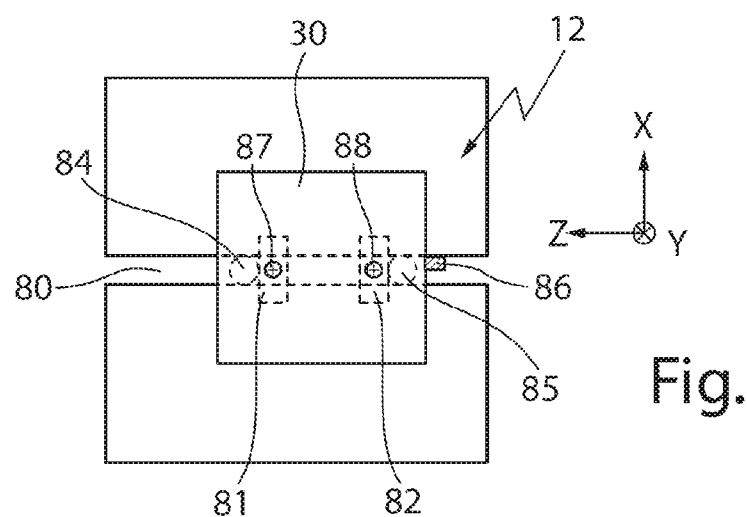
FIG. 11b shows a schematic side view of parts of the base structure according to FIG. 11a after mounting the reference body.

FIGS. 11a and 11b illustrate a reversible, accurate mounting of the reference body 30 on the base structure 12.

As shown in FIG. 11a, the base structure 12 has a guide 80 running parallel to the z direction, the guide being designed here as a gap or a groove. Two groove stones 81, 82 protrude from the back side into the guide. The groove stones 81, 82 are displaceable in the guide 80. The groove stones 81, 82 each have threaded holes 83.

The reference body 30 is movable in the guide 80 with two rear pins 84, 85. If the reference body 30 is moved to the right (here) in the guide 80, the reference body 30 will ultimately strike laterally against a stop element 86 of the base structure 12. FIG. 11b shows the corresponding end position.

In the end position, the groove stones 81, 82 can be moved in such a way that the two locking screws 87, 88 are arranged on the reference body 30 by means of the threaded holes in the groove stones 81, 82, so that the reference body 30 can be used by means of the locking screws 87, 88 on the groove stones 81, 82 and can thus be braced by means of the groove stones 81, 82 in the y direction. Then the reference body 30 is held in a stationary position on the whole.

Due to the guide 80 and the pins 84, 85, the reference body 30 is reproducibly and accurate placed in the x direction by the bracing on the base structure 12 in the y direction. The position in the z direction is predefined here by the stop element 86. It should be pointed out that for the adjustment of an X-ray diffractometer, the X-ray optics in the z direction need not be placed as accurately in the z direction as in the x and y directions. To remove the reference body 30, the locking screws 87, 88 may be released and the reference body removed from the guide 80.

Figure 12:
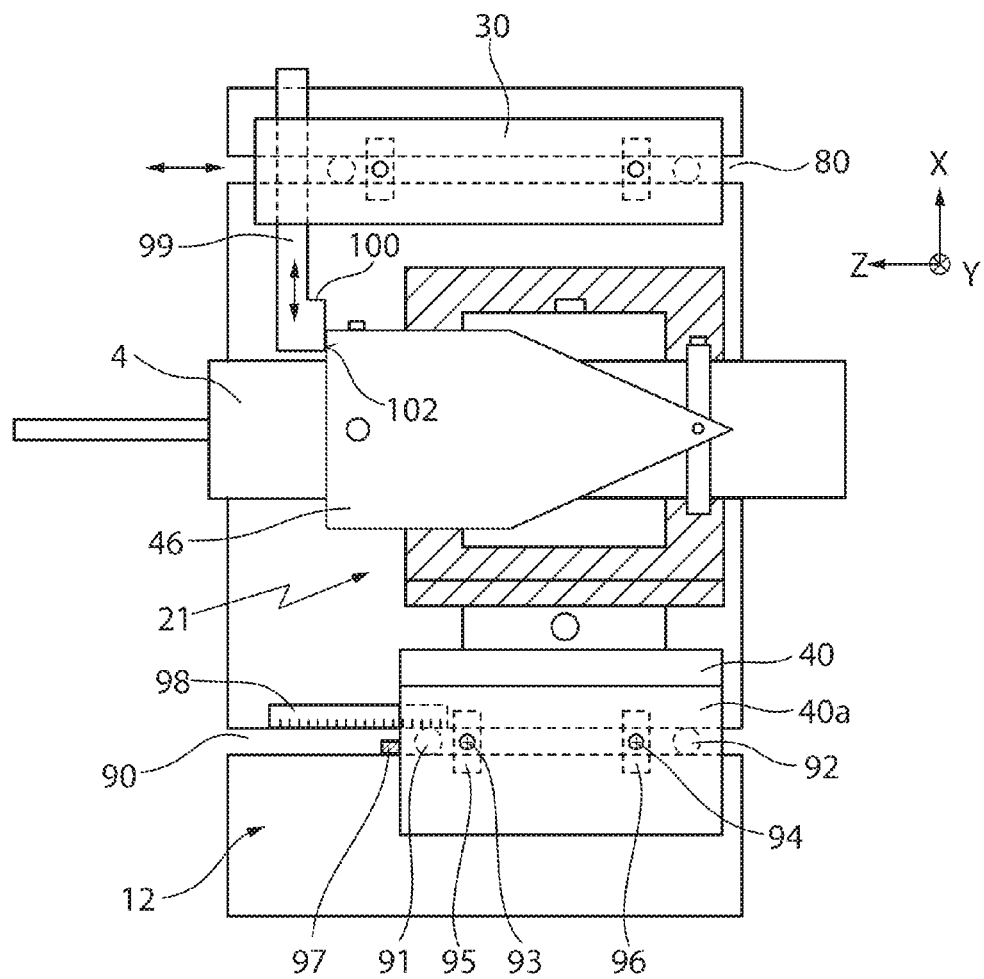
FIG. 12 shows a schematic side view of the base structure of the X-ray diffractometer with the reference body mounted and the holding device mounted.

FIG. 12 shows a side view of a part of the primary side 2 of FIG. 3 for illustration of the mounting of components on the base structure 12. In the upper third, a (reversible) mounting of the reference body 30 in the guide 80 can be seen, corresponding largely to the construction of FIGS. 11a, 11b. However, the stop element 99 here is formed on the reference body 30 and can be moved in the x direction. The stop element 99 sits with a nose 100 on the intermediate element 46 in the extracted position shown here. Opposing stop faces 102 of the nose 100 and intermediate element 46 lie parallel to the x and y directions so that a defined position of the reference body 30 in z direction can be assumed. The extractable stop element 99 makes it possible to align the reference body 30 in a defined manner with respect to the z direction in any adjustment positions in the x and y directions of the intermediate element 46. Typically, the reference body 30 is displaced along the guide 80 until the nose 100 of the stop element 99 comes to rest on the intermediate element 46. Then (rotating the z position of the reference body 30), the stop element 99 is retracted upward and the reference body 30 is secured by tightening the locking screws 87, 88. Due to this procedure it is ruled out that forces that could falsify the position of the X-ray optics 4 are transferred to the intermediate element 46 due to the stop element 99 in tightening of the locking screws 87, 88.

In a manner similar to that with reference body 30, the holding device 21 is also positioned on the base structure 12 with respect to the z direction. The holding device 21 here comprises a base element 40, which is mounted, in particular attached and clamped, onto a sub-base element 40a of the holding device 21 in a known and reversible manner by means of a pin connection, in particular a snap-lock connection or quick lock connection (not shown in greater detail here). The sub-base element 40a is in turn held in a base guide 90 running parallel to the z direction by means of pins 91, 92 and locking screws 93, 94 which are braced on the groove stones 95, 96. The x position of the holding device 21 is set by means of the pins 91, 92 and the base guide 90, and the y position of the holding device 21 is set by the bracing with the groove stones. The sub-base element 40a may be moved up to a (fixed) end stop 97 on the base structure 12. Alternatively, the z position of the sub-base element 40a may also be set using a scale 98. As already pointed out, the X-ray optics 4 need not be placed with as much accuracy in the z direction for adjustment of an X-ray diffractometer as that in the x and y directions.

Figure 13A:
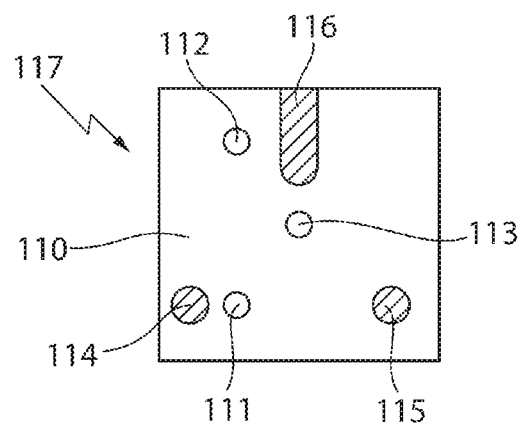
FIGS. 13a-c show schematic views of a plug element of a snap-lock connection for the invention, including a front view (13a), a side view (13b) and an oblique view (13c)
Figure 13B:
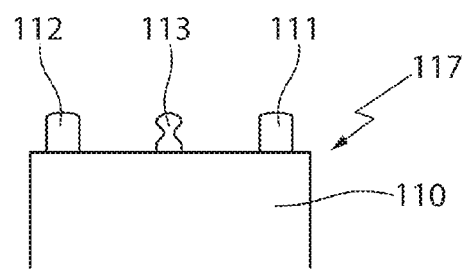
Figure 13C:
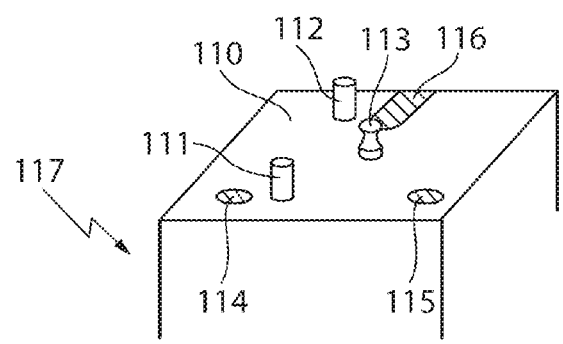

FIG. 13a (in a view from above), FIG. 13b (in a side view) and FIG. 13c (in an oblique view) show a plug element 110 of a clamp holder 117 according to the style of a snap-lock connection which can be used within the scope of the present invention for reversible but accurately positionable fastening of components (for example, the X-ray optics, the X-ray source or the collimator or a part of a collimator) in particular on the base structure. The snap-lock connection facilitates replacement of a single component in particular within the scope of an intermediate holder, by avoiding adjustment effort. An intermediate holder 18a may be used, for example, with the fastening device 18 for the housing 14 of the X-ray source 3 (cf. FIG. 8).

The plug element 110 here has two straight pins 111, 112 and a pinched pin 113 for locking, extending away from one side of the plug element 110 in a triangular arrangement. In addition, two round depressions (troughs) 114, 115 and an elongated depression (trough) 116 are provided on the same side. One of the round depressions 114, 115 is sunk in the form of a cone, and the other one of the depressions 114, 115 is sunk in the form of a cylinder. The depressions 114-116 form a first part of a three-point mount.

Figures 14A, 14B:
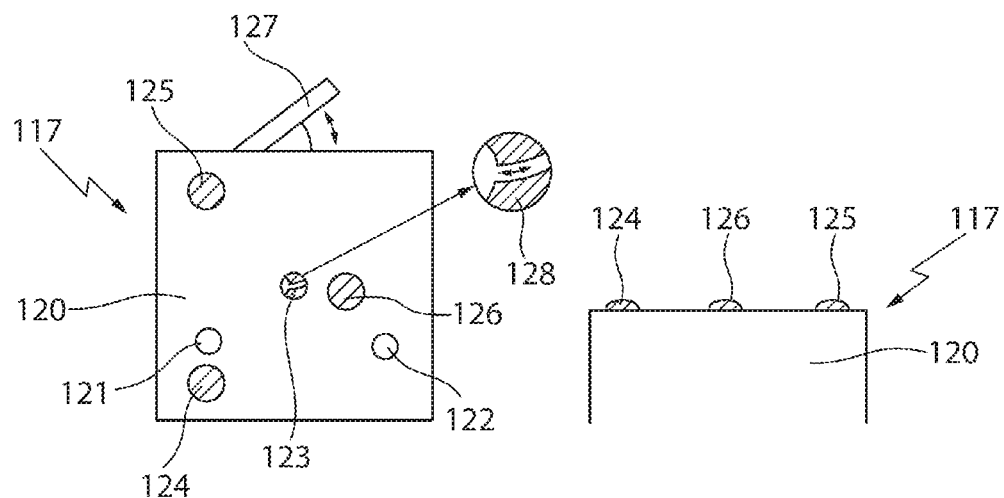
FIGS. 14a-c show schematic views of a clamping element of a snap-lock connection for the invention, including a front view (14a), a side view (14b) and an oblique view (14c)
Figure 14C:
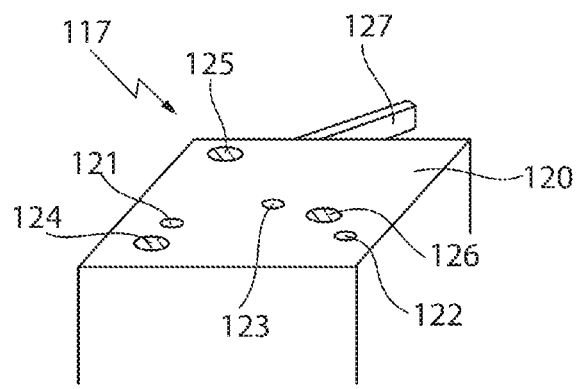

A clamping element 120 of the clamping holder 117 shown in FIG. 14a (in a view from above), in FIG. 14b (in a side view) and in FIG. 14c (in an oblique view) is designed with two holes 121, 122 for receiving the pins 111, 112 (see FIG. 13c) and with a hole 123 with a clamping function for receiving the pinched pin 113 (see FIG. 13c). Within the context of the snap-lock connection, a clamping device 128 with a recess can be pivoted by means of a lever 127 into the region of the hole 123, so that the plug element is pulled against the clamping element 120a by means of the pinched pin. Due to the fact that the lever 127 is flipped back and forth between two end positions, the clamping force of the clamping device 128 is precisely defined and reproducible.

In the case of a design of the clamping device 117 as a quick lock connection (not shown), the clamping force is not set by means of a lever but instead with the help of a torque wrench with a defined torque on a tension screw. A readily reproducible clamping force can also be obtained in this way.

In addition, three hemispherical protrusions 124, 125, 126 are formed on the clamping element 120, inserted into the depressions 114, 115, 116 (see FIG. 13c) and ensuring a self-centering effect for the defined mutual alignment of the plug element and the clamping element 120. The protrusions 124-126 form the second part of the three-point mount.

Figure 15A:
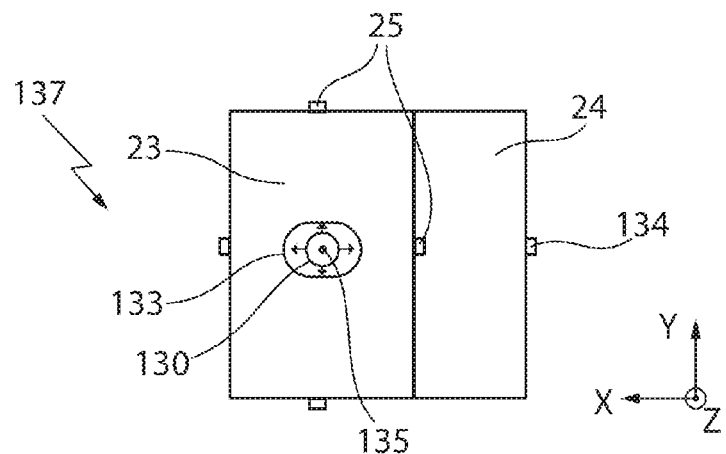
FIGS. 15a-c show schematic views of a collimator having a magnetic three-point mount, with a front view (15a), a side view (15b) and a rear view (15c)
Figure 15B:
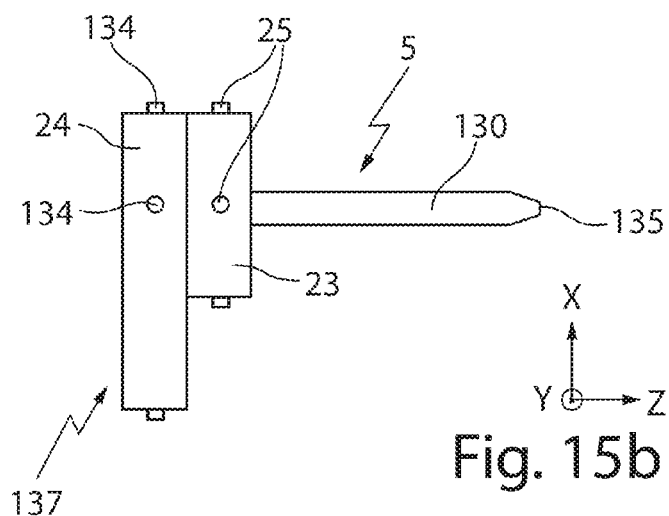
Figure 15C:
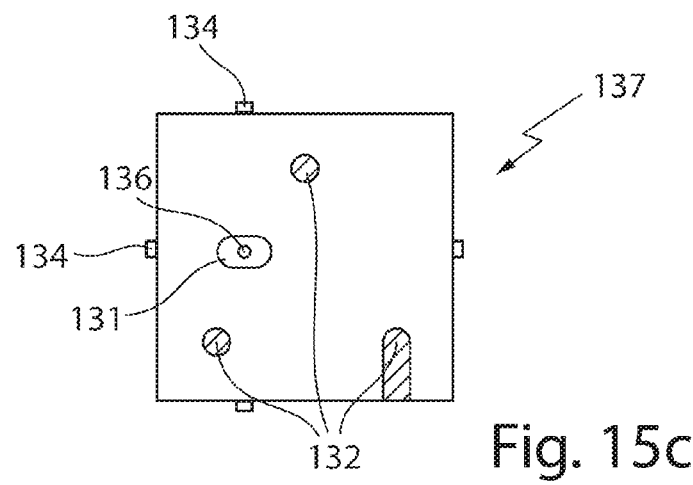

FIG. 15a (front view), FIG. 15b (side view) and FIG. 15c (rear view) show a magnetic holder 137 for the collimator 5 with a magnetic three-point mount which can be used within the scope of the invention. The collimator 5 must be removed occasionally as part of the adjustment according to invention and reinsert it so that the magnetic holder 137 is very suitable for this purpose. A magnetic three-point mount may also be used as part of an intermediate holder within the scope of the invention for reversible but accurately reproducible fastening of components (for example, the X-ray optics, the X-ray source or the collimator or a part of the collimator) in particular on the base structure.

The beam tube 130 of the collimator 5 is mounted on a base element 23 which allows adjustment of the position (translation in x, y) of the beam tube 130 upstream from a breakthrough 133 by means of adjusting screws 25. The tip of the beam tube 130 forms a first collimator aperture 135 and/or a first pinhole aperture (outlet opening) for the X-ray beam. The base element 23 is mounted on a holding element 24 which permits adjustment of the position (translation in x, y) of an aperture 131 using adjusting screws 134, with a second collimator aperture 136 and/or a second pinhole aperture. The holding element 24 is also equipped with a first part of a magnetic three-point mount 132 having two round depressions (sunk in the form of a cone in particular, on the one hand, and in the form of a cylinder, on the other hand) and an elongated depression on its rear side.

Figure 16A:
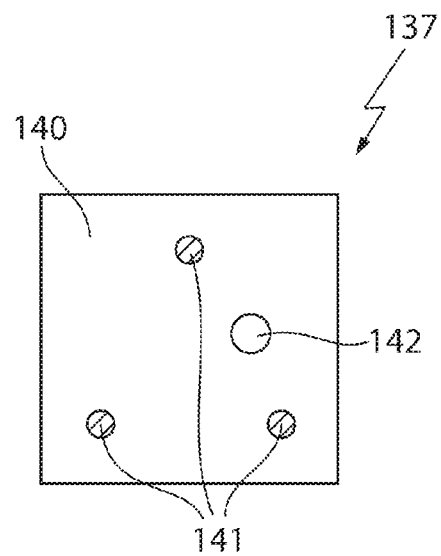
FIGS. 16a-b show schematic views of a mounting device for the collimator of FIGS. 15a-c with a counterpart of the magnetic three-point mount, with a view from above (16a) and a side view (16b)
Figure 16B:
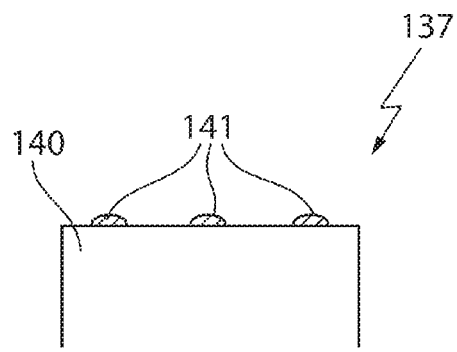

FIG. 16a (view from above) and FIG. 16b (frontal view) show a mounting device 140 of clamping holder 137 for the collimator in FIGS. 15a-15c. The mounting device 140 is typically fixedly connected to the base structure. It should be pointed out that the mounting device 140 can also be utilized for temporarily receiving a 2D detector.

The mounting device 140 forms the second part of a magnetic three-point mount 141 having three hemispherical protrusions. In the simplest case, the entire mounting device 140 is designed as a permanent magnet which attacks the at least partially ferromagnetic holding element. Alternatively, however, individual permanent magnets can also be integrated into the mounting device 140 and/or into the holding element. These magnets attract corresponding ferromagnetic or permanently magnetic parts toward one another. The hemispherical shape of the protrusions and depressions ensures a readily reproducible self-centering effect. The force of the permanent magnet(s) is practically fixed, so that the holding force is always the same in mutual contact of the holding element and the mounting device 140. An opening/bushing 142 for the X-ray beam is provided here in the mounting device 140. In alternative designs, the mounting device may extend over only a portion of the holding element, which does not include the X-ray beam path (not shown).

Figure 17:
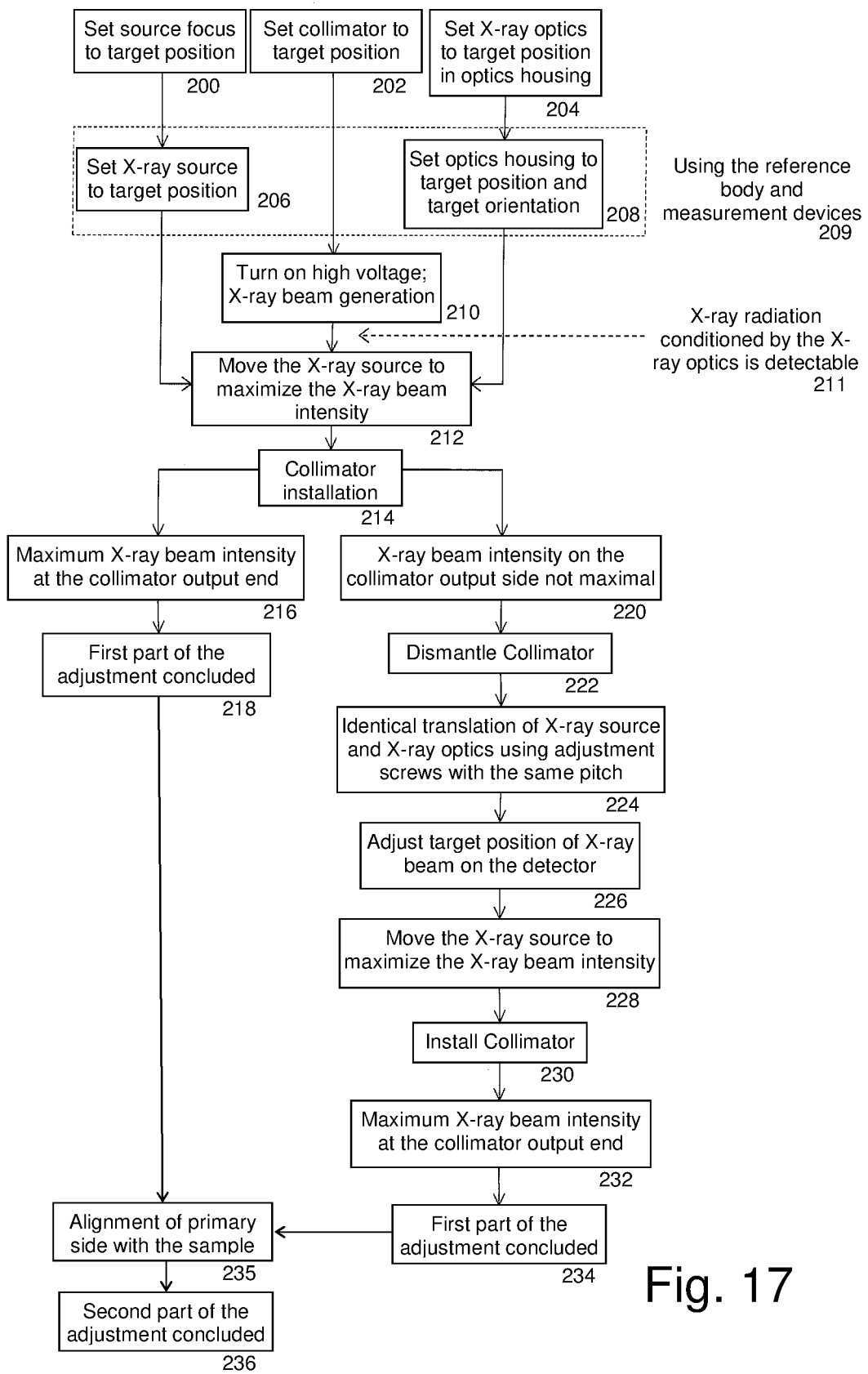
FIG. 17 shows a schematic flow chart of a variant of the method according to the invention for adjustment of the primary side of an X-ray diffractometer according to the teaching.

FIG. 17, for example, illustrates the sequence of a variant of the method according to the invention for adjusting the primary side of an X-ray diffractometer according to the invention, as shown in FIG. 1, for example. In a step 200 at the start of the adjustment, the position of the source focus of the X-ray source in the housing of the X-ray source is first set at a predetermined focus target value relative to the housing, if this is still necessary (the X-ray source is preferably already secured in the desired and/or predetermined focus target value at the manufacturers). Alternatively, the relative position of the source focus in the housing can also be measured, in particular relative to a target position, which yields a calibration correction for the subsequent setting of the X-ray source at its target value relative to the base structure.

In addition, in a step 202 the position of the collimator is set at a target value relative to the base structure. In doing so, the position of the collimator is typically measured and altered iteratively or continuously until reached the target value. As a rule, the reference body and one or more measurement devices here are used on the reference body (X-ray radiation is not necessary). Alternatively, in the case of an adjustable collimator, it is mounted with the required precision (typically accurate to 50 µm or better, preferably accurate to 20 µm or better).

Likewise, in a step 204, the X-ray optic in its housing is set at its predefined X-ray optic target values relative to the housing, inasmuch as this is still necessary (the X-ray optic has preferably been fixedly secured with the desired and/or presupposed X-ray optics target values at the manufacturer). Alternatively, the position and/or orientation relative to the housing can also be measured, in particular relative to a target position and/or to a target orientation, from which a calibration correction is derived for subsequent setting of the X-ray source at its target values. Step 204 may be omitted if the setting of the X-ray optics can be measured later through the housing.

In a step 206, the position of the X-ray source (and/or its housing) is set at its target value relative to the base structure. In doing so, the position is typically measured and/or determined and adjusted iteratively or continuously, relative to the base structure, until reaching the target value. Likewise, in a step 208, the position and orientation of the X-ray optics (and/or its housing) are set at their target values relative to the base structure. The position and/or orientation are also typically measured and/or determined and altered iteratively or continuously relative to the base structure until reaching the target values. For steps 206 and 208, the reference body is installed on the base structure and one or more measurement devices are used on the reference body (cf. note 209). After this, the reference body can be removed again.

The steps 206, 208 are typically carried out after the steps 200, 204. Step 202 can be carried out together with the steps 200, 204 or even (preferably) together with the steps 206, 208. Likewise, step 202 can also be postponed until after the conclusion of the precision adjustment of the X-ray source (cf. then step 214) or until after conclusion of the joint precision setting of the position of the X-ray source and the position of the X-ray optics and optionally again precision adjustment of the X-ray source (cf. then step 230). The setting of the respective target value takes place in steps 200, 202, 204, 206, 208 with an accuracy of 50 µm or better, preferably 20 µm or better (positions/distances) and/or of 1 mrad or better, preferably 0.5 mrad or better (orientations/angles).

After steps 206 and 208, the source focus of the X-ray source is situated approximately at a focus (focal point) of the X-ray optics which is typically designed with an elliptically curved Montel mirror or also a parabolically curved Montel mirror. In addition, the X-ray beam emanating from the X-ray source strikes the X-ray optics approximately at the Bragg angle, and the X-ray beam conditioned by the X-ray optics then preferably passes approximately centrally through one or more collimator apertures of the collimator.

Then, in a step 210, the high voltage is turned on at the X-ray source, so that an X-ray beam is generated by the X-ray source. Because of the preceding adjustment steps, X-ray radiation that has already been conditioned by the X-ray optic is detectable beyond the collimator (cf. note 211). If this is not the case, then errors from the preceding adjustment steps must be eliminated.

In a step 212, then by an iterative procedure (translation in x, y) of the movement of the X-ray source (and/or its housing) and checking of the intensity of the conditioned X-ray beam downstream from the X-ray optics, a maximization of the beam intensity is carried out. This precision adjustment of the position of the X-ray source is performed with the collimator dismantled in the variant presented here. In a precision setting, the position usually only changes by less than 200 µm, in most cases by less than 50 µm in the x and y directions.

In a step 214, the collimator can be installed again next. Often at this point in time a maximum X-ray beam intensity (or at least high enough for the planned application) has already been achieved downstream from the collimator (cf. step 216). In this case, the first part of the adjustment may be concluded (see step 218).

If the X-ray beam intensity downstream from the collimator is still not maximal (or at least not sufficient for the planned application), cf. step 220, the collimator is again dismantled in a step 222 in the preset variant and replaced by a calibrated 2D detector (preferably using a three-point mount on the base structure which can optionally hold the collimator or the 2D detector) in which a target position of the collimator aperture of the (replaced) collimator is marked. Then a joint precision setting of the position of the X-ray source and the position of the X-ray optic is performed (see step 224). For this purpose, the two positions are varied iteratively in concurrence, i.e., the position of the X-ray optics and the position of the X-ray source are adjusted by the same adjustment distances in the same direction in the same iterative step in smooth running until the X-ray beam is in the marked target position on the detector surface of the 2D detector. For example, the X-ray optics and the X-ray source are moved by 10 µm in the positive x direction in the same iteration step. For this purpose, an adjustment is made by the same angle (for example, exactly one revolution) on the respective adjusting screws which have the same thread pitch (for example, exactly one revolution). As a rule, the joint precision setting results only in changes in the position of less than 150 µm and mostly less than 50 µm in the x and y directions. Finally, if the X-ray beam is situated in the marked target position (cf. step 226), the X-ray beam intensity downstream from the collimator would be maximized if one would introduce it again into the beam path.

As an alternative to steps 224 and 226, in the case of an adjustable collimator, a precision adjustment of the position of the collimator and/or at least one pinhole aperture of the collimator may also take place in order to maximize the beam intensity beyond the collimator.

In the variant shown here, after the joint precision setting 224 and reaching the target position of the X-ray beam 226, an additional precision setting of the position of the X-ray source 228 alone is performed. In this process, the position of the X-ray source is again varied iteratively until the conditioned X-ray beam intensity downstream from the X-ray optic is at its maximum. As a rule, only minor changes in the position of less than 20 μm and mostly less than 10 μm in x and y directions are made in this second precision adjustment.

Next the collimator is installed (cf. step 230) and a maximum X-ray intensity is established downstream from the collimator (cf. step 232). If desired, the current position and orientation of the X-ray optics and the current position of the X-ray source and optionally also the current position of the collimator and/or at least one pinhole aperture may be noted, if desired, to be able to retrieve the found adjustment setting rapidly in the event of a misalignment. Thus, the first part of the adjustment method according to the invention is thereby concluded (cf. step 234).

In practice then if necessary the primary side may be aligned accurately with the sample as a whole (cf. step 235), for example, by moving or pivoting the base structure with respect to a foot element that is connected to the goniometer. After this, the second part of the adjustment method according to the invention is thereby concluded (cf. step 236).

In summary the present invention describes an adjustment concept for the primary side of an X-ray diffractometer, in particular a single crystal X-ray diffractometer having a microfocus X-ray source, and a respective X-ray diffractometer. The components of the primary side (X-ray source, X-ray optics and preferably also the collimator) are positioned and oriented individually with respect to a common base structure by moving the components to geometrically predetermined target positions and/or to geometrically determined target orientations, preferably with an accuracy in the range of 50 μm or better, preferably 20 μm or better at each measurement site. No X-ray beam is needed for this so these adjustment steps can be carried out easily, quickly and reliably. For discovering the target positions and/or target orientations, measurement devices (usually installed temporarily) which can determine the location and/or alignment of the components or parts thereof relative to the base structure are used, in particular distance measuring devices. After these adjustment steps an X-ray beam can be discovered easily and reliably downstream from the collimator so that any further adjustment steps for maximization of intensity (then with the X-ray beam turned on) can then be performed rapidly. A typical X-ray diffractometer for the invention includes a (stationary) microfocus X-ray tube, a Montel multi-layer X-ray mirror ("Montel mirror"), a collimator, a base structure having a collimator holder, a goniometer having at least one motorized rotational axis, on which is situated a sample holder, which can be centered with respect to the axis (axes) of rotation, and having a planar detector for detecting the X-ray radiation diffracted by the sample, wherein the collimator is connected mechanically to the collimator holder (and thus to the base structure) due to translational adjustments (for precision adjustment of its position) wherein the Montel mirror is mechanically linked to the base structure via translation and rotational adjustments (so that the Montel mirror can be set at a setting of at least 0.05° according to its ideal Bragg angle and the ideal position can be set to an accuracy of at least 0.1 mm) wherein the X-ray tube is mechanically linked to the base structure by means of translational adjustments (so that the X-ray tube can be brought into the primary focus of the Montel mirror by means of the translations and wherein the base structure is connected to the goniometer mechanically by means of translational and/or rotational adjustments so that the X-ray beam can be directed at the sample).

The invention claimed is:

1. A method for adjusting a primary side of an X-ray diffractometer wherein the primary side comprises a collimator, X-ray optics, and an X-ray source mounted on a base structure, an orientation and position of the X-ray optics and a position of the X-ray source being adjustable relative to the base structure, wherein the orientation and position of the X-ray optics and the position of the X-ray source relative to the base structure are measured and set at predetermined optics and source target values, respectively, and wherein after setting the predefined optics and source target values, a common precision adjustment of the position of the X-ray source and the position of the X-ray optics is performed in which the beam intensity at the output end of the collimator is maximized, wherein the X-ray optics and the X-ray source are each moved by the same distances in the same directions between two intensity measurements.

2. The method according to claim 1, wherein the orientation of the X-ray optics is measured and set with an accuracy of 1 mrad or better, and the positions of the X-ray optics and of the X-ray source are measured and set with an accuracy of 50 μm or better.

3. The method according to claim 1, wherein
   the orientation and position of the X-ray optics relative to the base structure and
   the position of the X-ray source relative to the base structure are set independently of one another.

4. The method according to claim 1, wherein the position of the X-ray source and the position and orientation of the X-ray optics are measured by distance measurements.

5. The method according to claim 1 wherein the position and orientation of the X-ray optics are adjusted by adjusting the position and orientation of a housing of the X-ray optics in which the X-ray optics are arranged in a known position and orientation, and to determine the position and orientation of the X-ray optics, the position and orientation of the housing of the X-ray optics are measured.

6. The method according to claim 1, wherein the X-ray optics are arranged in a housing, wherein said housing is manufactured, at least in part, from optically transparent material, and the measurement of the position and the orientation of the X-ray optics is performed through the optically transparent material.

7. The method according to claim 1, wherein the position of the X-ray source is adjusted in two linearly independent directions (x, y) perpendicular to the beam propagation direction (z) relative to the base structure, and the position of the X-ray optics is adjusted in two linearly independent directions (x, y) perpendicular to the beam propagation direction (z), and the orientation of the X-ray optics with respect to two axes (A, B) is adjusted perpendicular to the beam propagation direction (z) relative to the base structure.

8. The method according to claim 1 wherein the collimator comprises at least one collimator aperture a position of which is measured relative to the base structure and is set at a predetermined collimator target value.

9. The method according to claim 8, wherein the position of the at least one collimator aperture of the collimator is adjusted independently of the position of the X-ray source and the position and orientation of the X-ray optics.

10. The method according to claim 1, wherein the collimator comprises at least one collimator aperture and wherein said common precision adjustment comprises a common precision adjustment of the position of the X-ray source, the position of the X-ray optics and the position of the at least one collimator aperture.

11. The method according to claim 1, wherein the source is located in a source housing and wherein, before adjusting the predefined optics and source target values, a position of the X-ray source is adjusted by adjusting a position of the source housing, and for determining the position of the X-ray source, the position of the source housing is measured.

12. The method according to claim 1, wherein, after adjusting the predefined optics and source target values, the orientation and position of the X-ray optics and the position of the X-ray source are measured again relative to the base structure and the respective measured data are recorded, and after a misalignment of one or more components any misaligned components are adjusted according to the recorded measured data relative to the base structure.

13. The method according to claim 1, wherein the primary side as a whole is aligned with the sample by moving or pivoting the base structure with respect to a foot element that is connected to a goniometer.

14. An X-ray diffractometer comprising a primary side having a collimator, X-ray optics and an X-ray source, wherein the collimator, the X-ray optics and the X-ray source are mounted on a base structure, wherein an orientation and position of the X-ray optics and a position of the X-ray source are adjustable relative to the base structure by adjustment devices, and wherein the X-ray diffractometer further comprises one or more measurement devices with which the orientation and position of the X-ray optics and the position of the X-ray source are determined relative to the base structure, the one or more measurement devices being arranged on a reference body that is reversibly mounted on the base structure.

15. The X-ray diffractometer according to claim 14, wherein the one or more measurement devices have a measurement accuracy for the orientation of the X-ray optics of 1 mrad or better and have a measurement accuracy for the positions of the X-ray optics and of the X-ray source of 50 µm or better.

16. The X-ray diffractometer according to claim 14, wherein the one or more measurement devices comprise a mechanical scanning element and/or a laser distance measurement element.

17. The X-ray diffractometer according to claim 14, wherein the X-ray optics comprise at least one of a Montel mirror and a Goebel mirror.

18. The X-ray diffractometer according to claim 14, wherein the X-ray source is designed with one of:
    a microfocus X-ray tube,
    a rotary anode X-ray tube or
    a liquid metal X-ray tube.

19. The X-ray diffractometer according to claim 14, wherein the reference body is a single one-piece component.

20. The X-ray diffractometer according to claim 14, wherein the reference body is pushed onto a guide on the base structure and is locked on the base structure at a position at which pushing of the reference body onto the guide is stopped by a stop element is provided on one of the base structure and the reference body.

21. The X-ray diffractometer according to claim 20, wherein the X-ray optics is are mounted on the base structure by means of a holding device a base element of which is movable along a base guide that runs in the beam propagation direction (z) and lockable to the base structure, and wherein an intermediate element of the holding device is adjustable with respect to the base element in two mutually perpendicular directions (x, y), which run perpendicular to the beam propagation direction (z), hereinafter referred to as the first direction (x) and the second direction (y), the X-ray optics being tiltable relative to the intermediate element about two mutually perpendicular axes (A, B), which run perpendicular to the beam propagation direction (z), and the stop element of the reference body being extractable toward the intermediate element along the first direction (x), wherein the intermediate element and the stop element form mutual stop faces parallel to the first and second direction (x, y).

22. The X-ray diffractometer according to claim 14, wherein the X-ray diffractometer has a foot element, and wherein a position and/or orientation of the base structure is adjustable with respect to the foot element.

23. The X-ray diffractometer according to claim 14, wherein the collimator, the X-ray optics and the X-ray source are mounted independently of one another on the base structure and a separate adjusting device is provided for each of the X-ray optics and the X-ray source, so that
    the orientation and position of the X-ray optics relative to the base structure
    and the position of the X-ray source relative to the base structure are adjustable independently of one another.

24. The X-ray diffractometer according to claim 23, wherein at least one of the X-ray optics, the X-ray source and the collimator is is/are mounted reversibly on an intermediate holder, and each intermediate holder is adjustable individually with respect to the base structure by means of a separate adjusting device.

25. The X-ray diffractometer according to claim 14, wherein the adjustment devices for adjusting the position of the X-ray source and for adjusting the position of the X-ray optics are each designed as adjusting screws having a common thread pitch in a respective direction.

\* \* \* \* \*